United States Patent
Gualtieri et al.

(10) Patent No.: US 9,260,481 B2
(45) Date of Patent: Feb. 16, 2016

(54) PEPTIDE DERIVATIVES AS ANTIBIOTICS

(71) Applicants: Maxime Gualtieri, Gallargues le Montueux (FR); Philippe Villain-Guillot, Montpellier (FR); Alain Givaudan, Saint Mathieu de Treviers (FR); Sylvie Pages, Saint Clement de Riviere (FR)

(72) Inventors: Maxime Gualtieri, Gallargues le Montueux (FR); Philippe Villain-Guillot, Montpellier (FR); Alain Givaudan, Saint Mathieu de Treviers (FR); Sylvie Pages, Saint Clement de Riviere (FR)

(73) Assignees: Nosopharm (FR); Institut National de la Recherche Agronomique (FR)

( * ) Notice: Subject to any disclaimer, the term of this patent is extended or adjusted under 35 U.S.C. 154(b) by 35 days.

(21) Appl. No.: 14/342,446

(22) PCT Filed: Sep. 28, 2012

(86) PCT No.: PCT/EP2012/069166
§ 371 (c)(1),
(2) Date: Mar. 3, 2014

(87) PCT Pub. No.: WO2013/045600
PCT Pub. Date: Apr. 4, 2013

(65) Prior Publication Data
US 2015/0175659 A1  Jun. 25, 2015

Related U.S. Application Data

(60) Provisional application No. 61/540,085, filed on Sep. 28, 2011.

(30) Foreign Application Priority Data

Sep. 28, 2011  (EP) .................................... 11183034

(51) Int. Cl.
| | |
|---|---|
| *C07K 7/06* | (2006.01) |
| *A61K 38/08* | (2006.01) |
| *C12P 21/02* | (2006.01) |
| *C12R 1/01* | (2006.01) |
| *A61K 45/06* | (2006.01) |
| *A61K 38/00* | (2006.01) |

(52) U.S. Cl.
CPC . *C07K 7/06* (2013.01); *A61K 38/08* (2013.01); *A61K 45/06* (2013.01); *C12P 21/02* (2013.01); *C12R 1/01* (2013.01); *A61K 38/00* (2013.01)

(58) Field of Classification Search
None
See application file for complete search history.

(56) References Cited

U.S. PATENT DOCUMENTS

2011/0033389 A1* 2/2011 Chen .................... C07K 16/087
424/9.6

FOREIGN PATENT DOCUMENTS

| GB | 2207433 A | 2/1989 |
| WO | 02055545 A1 | 7/2002 |
| WO | 2010136532 A1 | 12/2010 |

OTHER PUBLICATIONS

Wang et al., Enhanced antibiotic activity of Xenorhabdus nematophila by medium optimization, Bioresource Tech, 99 (2008) 1708-1715.*
GenBank: AAM02072.1, RNA-binding protein involved in rRNA processing, of Methanopyrus kandleri AV19, Jan. 2014.*
Identification of a new antimicrobial lysine-rich cyclolipopeptide family from Xenorhabdus nematophila, Gualtieri et al., Jl. Of Antibiotics, (2009) 62, 295-302.*
Berdy Janos, et al., "Bioactive Microbial Metabolites," The Journal of Antibiotics, 2005, pp. 1-26, vol. 58, No. 1.
Bodanszky, M., The Practice of Peptide Synthesis, Reactivity and Structure Concepts in Organic Chemistry, Springer Laboratory, 1994, 16 pages.
Forst, S., et al., Molecular Biology of the Symbiotic-Pathogenic Bacteria *Xenorhabdus* spp. and *Photorhabdus* spp., American Society for Microbiology, Mar. 1, 1996, pp. 21-43.
Marion, D., et al., Rapid Recording of 2D NMR Spectra without Phase Cycling. Application to the Study of Hydrogen Exchange in Proteins, Journal of Magnetic Resonance, Jul. 25, 1989, pp. 393-399.
Nolden, S., et al., Analysis of RegA, a Pathway-Specific Regulator of the Friulimincin Biosynthesis in Actinoplanes Friuliensis, Journal of Biotechnology, Mar. 10, 2009, vol. 140, No. 1-2, pp. 99-106.
Piotto, M., et al., Gradient-Tailored Excitation for Single-Quantum NMR Spectroscopy of Aqueous Solutions, Journal of Biomolecular NMR, Oct. 15, 1992, pp. 661-665.

* cited by examiner

*Primary Examiner* — Karlheinz R Skowronek
*Assistant Examiner* — Joseph Fischer
(74) *Attorney, Agent, or Firm* — Banner & Witcoff, Ltd.

(57) ABSTRACT

The present invention relates to antibiotic compounds, methods for producing said compounds, pharmaceutical compositions comprising said compounds, and methods of treatment comprising administering said compounds and/or compositions comprising said compounds.

9 Claims, 4 Drawing Sheets

```
                       SEQUENCE LISTING

<160> NUMBER OF SEQ ID NOS: 3

<210> SEQ ID NO 1
<211> LENGTH: 10
<212> TYPE: PRT
<213> ORGANISM: Xenorhabdus nematophilus
<220> FEATURE:
<221> NAME/KEY: MISC_FEATURE
<222> LOCATION: (2)..(2)
<223> OTHER INFORMATION: 3-hydroxy-2,4-diaminobutanoic acid
<220> FEATURE:
<221> NAME/KEY: MISC_FEATURE
<222> LOCATION: (3)..(3)
<223> OTHER INFORMATION: 3-hydroxy-2,4-diaminobutanoic acid
<220> FEATURE:
<221> NAME/KEY: MISC_FEATURE
<222> LOCATION: (5)..(5)
<223> OTHER INFORMATION: Ornithine
<220> FEATURE:
<221> NAME/KEY: MISC_FEATURE
<222> LOCATION: (8)..(8)
<223> OTHER INFORMATION: 5-hydroxylysine
<220> FEATURE:
<221> NAME/KEY: MISC_FEATURE
<222> LOCATION: (9)..(9)
<223> OTHER INFORMATION: 2,3-dehydroarginine
<220> FEATURE:
<221> NAME/KEY: MISC_FEATURE
<222> LOCATION: (10)..(10)
<223> OTHER INFORMATION: 5-hydroxylysine

<400> SEQUENCE: 1

Lys Xaa Xaa Gly Xaa Pro His Xaa Xaa Xaa
1               5                  10

<210> SEQ ID NO 2
<211> LENGTH: 10
<212> TYPE: PRT
<213> ORGANISM: Xenorhabdus nematophilus
<220> FEATURE:
<221> NAME/KEY: MISC_FEATURE
<222> LOCATION: (2)..(2)
<223> OTHER INFORMATION: 3-hydroxy-2,4-diaminobutanoic acid
```

```
<220> FEATURE:
<221> NAME/KEY: MISC_FEATURE
<222> LOCATION: (3)..(3)
<223> OTHER INFORMATION: 3-hydroxy-2,4-diaminobutanoic acid
<220> FEATURE:
<221> NAME/KEY: MISC_FEATURE
<222> LOCATION: (5)..(5)
<223> OTHER INFORMATION: Ornithine
<220> FEATURE:
<221> NAME/KEY: MISC_FEATURE
<222> LOCATION: (9)..(9)
<223> OTHER INFORMATION: 2,3-dehydroarginine
<220> FEATURE:
<221> NAME/KEY: MISC_FEATURE
<222> LOCATION: (10)..(10)
<223> OTHER INFORMATION: 5-hydroxylysine

<400> SEQUENCE: 2

Lys Xaa Xaa Gly Xaa Pro His Lys Xaa Xaa
1               5                   10

<210> SEQ ID NO 3
<211> LENGTH: 10
<212> TYPE: PRT
<213> ORGANISM: Xenorhabdus nematophilus
<220> FEATURE:
<221> NAME/KEY: MISC_FEATURE
<222> LOCATION: (2)..(2)
<223> OTHER INFORMATION: 3-hydroxy-2,4-diaminobutanoic acid
<220> FEATURE:
<221> NAME/KEY: MISC_FEATURE
<222> LOCATION: (3)..(3)
<223> OTHER INFORMATION: 3-hydroxy-2,4-diaminobutanoic acid
<220> FEATURE:
<221> NAME/KEY: MISC_FEATURE
<222> LOCATION: (5)..(5)
<223> OTHER INFORMATION: Ornithine
<220> FEATURE:
<221> NAME/KEY: MISC_FEATURE
<222> LOCATION: (9)..(9)
<223> OTHER INFORMATION: 2,3-dehydroarginine

<400> SEQUENCE: 3

Lys Xaa Xaa Gly Xaa Pro His Lys Xaa Lys
1               5                   10
```

PEPTIDE DERIVATIVES AS ANTIBIOTICS

RELATED APPLICATION DATA

This application is a National Stage Application under 35 U.S.C. 371 of co-pending PCT application PCT/EP2012/069166 designating the United States and filed Sep. 28, 2012; which claims the benefit of EP application number 11183034.5 and filed Sep. 28, 2011 each of which are hereby incorporated by reference in their entireties.

FIELD OF THE INVENTION

The present invention relates to new antibiotic compounds and compositions comprising the same, to a strain of *Xenorhabdus nematophila* capable of producing said antibiotic compounds, and to the use of such compounds and compositions thereof in the treatment of microbial disease.

BACKGROUND OF THE INVENTION

Antimicrobial resistance is a major public health problem with a significant impact on morbidity, mortality and healthcare-associated costs. The problem has been worsened by the restriction of antibiotic drug discovery and development programs. Nowadays, the most relevant multiresistant bacterial pathogens are methicillin-resistant *Staphylococcus aureus* (MRSA), vancomycin-resistant *enterococci* (VRE), extended spectrum β-lactamase formers (ESBL), multiresistant *Pseudomonas* and *Acinetobacter* species. For these bacteria, only a few of the existing antibiotics are efficient. There is an urgent need for new antibacterial compounds to ensure that bacterial infections can be effectively treated in the future. Living organisms have proven to be a reliable source of bioactive chemicals with antimicrobial activity (Berdy J., *J. Antibiot.* 58, 1-26 (2005)). Environmental microbes continue to be promising resources for the identification of new molecules.

SUMMARY OF THE INVENTION

In one aspect, the present invention is related to a compound of formula (I):

$$\text{Xaa}_1\text{-Xaa}_2\text{-Xaa}_3\text{-Xaa}_4\text{-Xaa}_5\text{-Xaa}_6\text{-Xaa}_7\text{-Xaa}_8\text{-Xaa}_9\text{-Xaa}_{10}\text{-NH--(CH}_2)_n\text{--R} \quad (I)$$

wherein $Xaa_1$, $Xaa_2$, $Xaa_3$, $Xaa_5$, $Xaa_7$, $Xaa_8$ and $Xaa_{10}$ are independently selected from the group consisting of lysine, 3-hydroxylysine, 4-hydroxylysine, 5-hydroxylysine, 3,4-dihydroxylysine, 3,5-dihydroxylysine, 4,5-dihydroxylysine, ornithine, 3-hydroxyornithine, 4-hydroxyornithine, 3,4-dihydroxyornithine, 2,4-diaminobutanoic acid, 3-hydroxy-2,4-diaminobutanoic acid, arginine, histidine, serine, and threonine;

$Xaa_4$ is glycine, 3-aminopropanoic acid, or 4-aminobutanoic acid;

$Xaa_6$ is proline, 3-hydroxyproline, 4-hydroxyproline, aziridine-2-carboxylic acid, azetidine-2-carboxylic acid, pipecolic acid, 4-oxaproline, 3-thiaproline, 4-thiaproline, 3,4-dehydroproline, 4-aminoproline, 4-fluoroproline, α-methylproline, or α-allylproline;

$Xaa_9$ is arginine, 2,3-dehydroarginine, citrulline, 2,3-dehydrocitrulline, canavanine, or 2,3-dehydrocanavanine;

n is 2, 3, 4, 5, 6, 7, 8, 9, or 10; and

R is —OH, —NH$_2$, or —COOH.

In one embodiment, $Xaa_1$ is lysine; $Xaa_2$ and $Xaa_3$ are each 3-hydroxy-2,4-diaminobutanoic acid; $Xaa_4$ is glycine; $Xaa_5$ is ornithine; $Xaa_6$ is proline; $Xaa_7$ is histidine; and $Xaa_9$ is 2,3-dehydroarginine.

In another embodiment, $Xaa_1$ is lysine; $Xaa_2$ and $Xaa_3$ are each 3-hydroxy-2,4-diaminobutanoic acid; $Xaa_4$ is glycine; $Xaa_5$ is ornithine; $Xaa_6$ is proline; $Xaa_7$ is histidine; $Xaa_8$ is lysine or 5-hydroxylysine; $Xaa_9$ is 2,3-dehydroarginine; and $Xaa_{10}$ is lysine or 5-hydroxylysine.

In another embodiment, $Xaa_1$ is lysine; $Xaa_2$ and $Xaa_3$ are each 3-hydroxy-2,4-diaminobutanoic acid; $Xaa_4$ is glycine; $Xaa_5$ is ornithine; $Xaa_6$ is proline; $Xaa_7$ is histidine; $Xaa_8$ is lysine or 5-hydroxylysine; $Xaa_9$ is 2,3-dehydroarginine; $Xaa_{10}$ is lysine or 5-hydroxylysine; n is 4; and R is NH$_2$.

In a preferred embodiment, the present invention is related to a compound of formula (Ia):

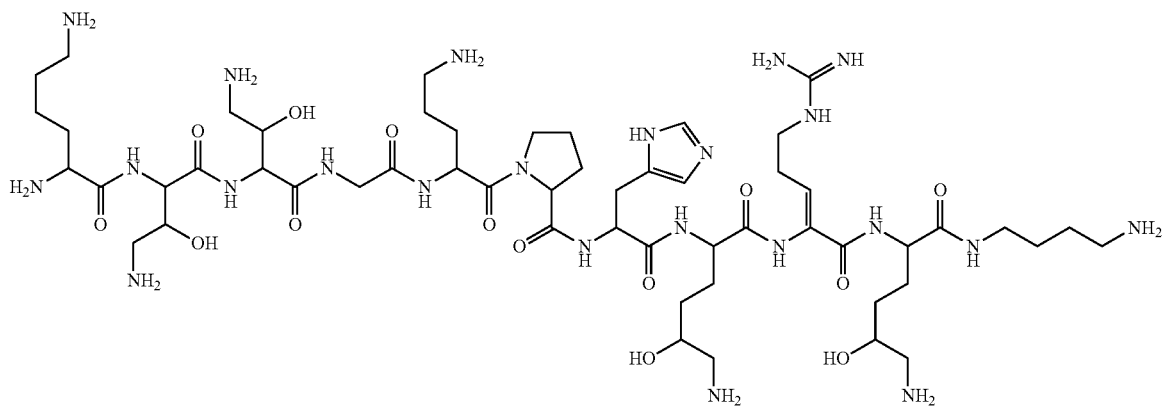 [SMILES: N=C(N)NCC/C=C(\NC(=O)C(CCC(O)CN)NC(=O)C(Cc1cnc[nH]1)NC(=O)C1CCCN1C(=O)C(CCCN)NC(=O)CNC(=O)C(NC(=O)C(NC(=O)C(N)CCCCN)C(O)CN)C(O)CN)C(=O)NC(CCC(O)CN)C(=O)NCCCCN]

In another preferred embodiment, the invention is related to a compound of formula (Ib):

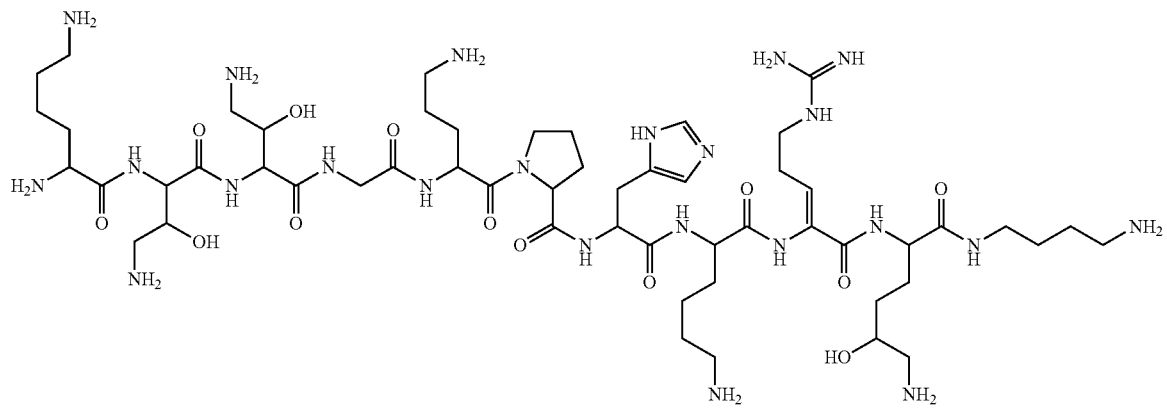 [SMILES: N=C(N)NCC/C=C(\NC(=O)C(CCCCN)NC(=O)C(Cc1cnc[nH]1)NC(=O)C1CCCN1C(=O)C(CCCN)NC(=O)CNC(=O)C(NC(=O)C(NC(=O)C(N)CCCCN)C(O)CN)C(O)CN)C(=O)NC(CCC(O)CN)C(=O)NCCCCN]

In another preferred embodiment, the invention is related to a compound of formula (Ic):

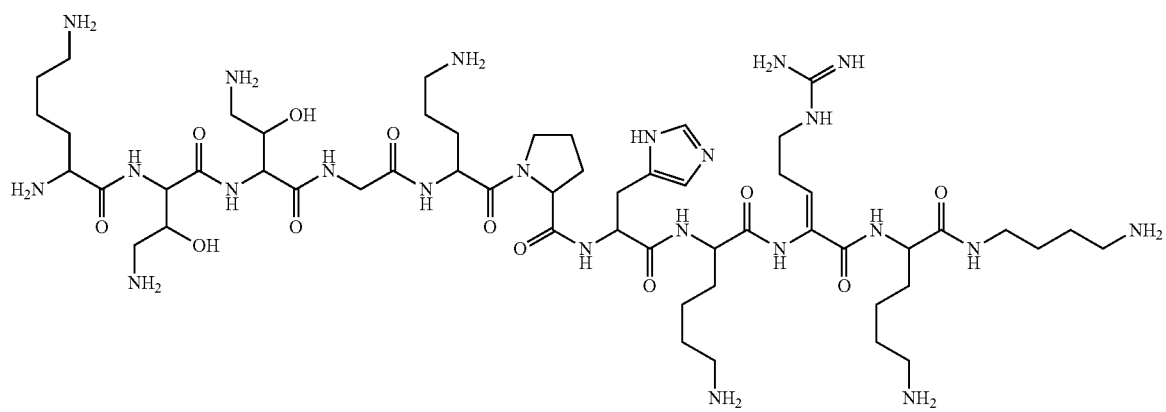 [SMILES: N=C(N)NCC/C=C(\NC(=O)C(CCCCN)NC(=O)C(Cc1cnc[nH]1)NC(=O)C1CCCN1C(=O)C(CCCN)NC(=O)CNC(=O)C(NC(=O)C(NC(=O)C(N)CCCCN)C(O)CN)C(O)CN)C(=O)NC(CCCCN)C(=O)NCCCCN]

In another aspect, the present invention is related to a compound wherein the compound is not (Ia), (Ib), or (Ic).

Preferably, the compounds of the present invention are isolated. Preferably, the compound is greater than about 90% pure. More preferably, the compound is greater than about 95% pure. Even more preferably, the compound is greater than about 98% pure. Even more preferably, the compound is greater than about 99% pure.

The present invention is also directed to a pharmaceutical composition comprising a compound as described above and a pharmaceutically acceptable carrier.

Preferably, the pharmaceutical composition further comprises a second antibiotic compound. Preferably, the second antibiotic compound is an aminoglycoside antibiotic. Preferably, the second antibiotic compound is kanamycin. Preferably, the second antibiotic compound is gentamicin.

The present invention is also directed to a method for treating bacterial infection in a subject comprising administration of a therapeutically effective amount of a compound of formula (I):

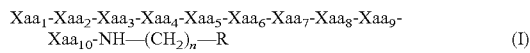

wherein, $Xaa_1$, $Xaa_2$, $Xaa_3$, $Xaa_5$, $Xaa_7$, $Xaa_8$ and $Xaa_{10}$ are independently selected from the group consisting of lysine, 3-hydroxylysine, 4-hydroxylysine, 5-hydroxylysine, 3,4-dihydroxylysine, 3,5-dihydroxylysine, 4,5-dihydroxylysine, ornithine, 3-hydroxyornithine, 4-hydroxyornithine, 3,4-dihydroxyornithine, 2,4-diaminobutanoic acid, 3-hydroxy-2,4-diaminobutanoic acid, arginine, histidine, serine, and threonine;

$Xaa_4$ is glycine, 3-aminopropanoic acid, or 4-aminobutanoic acid;

$Xaa_6$ is proline, 3-hydroxyproline, 4-hydroxyproline, aziridine-2-carboxylic acid, azetidine-2-carboxylic acid, pipecolic acid, 4-oxaproline, 3-thiaproline, 4-thiaproline, 3,4-dehydroproline, 4-aminoproline, 4-fluoroproline, α-methylproline, or α-allylproline;

$Xaa_9$ is arginine, 2,3-dehydroarginine, citrulline, 2,3-dehydrocitrulline, canavanine, or 2,3-dehydrocanavanine;

n is 2, 3, 4, 5, 6, 7, 8, 9, or 10; and

R is —OH, —NH$_2$, or —COOH, or a composition comprising a compound of formula (I) and a pharmaceutically acceptable carrier, to a subject in need thereof.

In the methods of the present invention it is preferred that $Xaa_1$ is lysine; $Xaa_2$ and $Xaa_3$ are each 3-hydroxy-2,4-diaminobutanoic acid; $Xaa_4$ is glycine; $Xaa_5$ is ornithine; $Xaa_6$ is proline; $Xaa_7$ is histidine; $Xaa_8$ is lysine or 5-hydroxylysine; $Xaa_9$ is 2,3-dehydroarginine; $Xaa_{10}$ is lysine or 5-hydroxylysine; n is 4; and R is NH$_2$.

In the methods of the present invention it is preferred that the compound of formula (I) is:

(Ia)

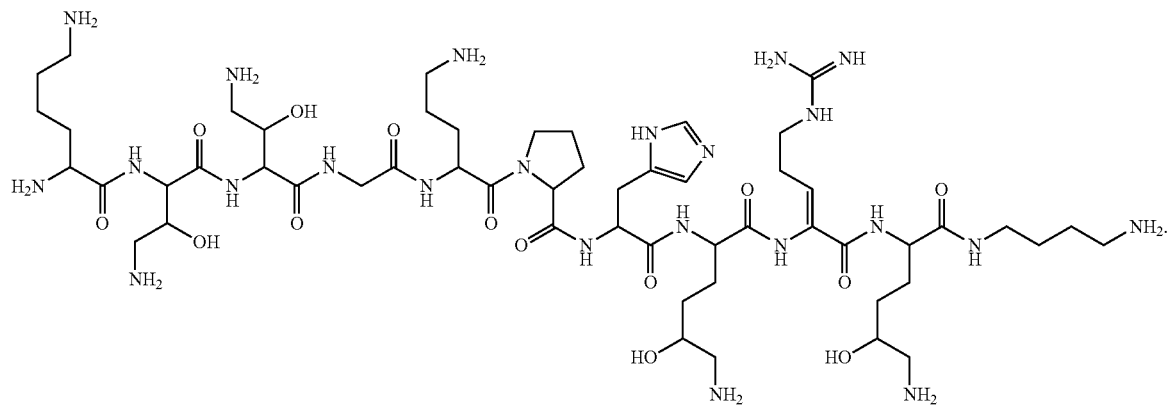

Preferably, the methods of the present invention comprise administration of a second antibiotic compound. Preferably, the second antibiotic compound is an aminoglycoside antibiotic. Preferably, the second antibiotic compound is kanamycin. Preferably, the second antibiotic compound is gentamicin.

In the methods of the present invention, the subject is preferably a mammal. Preferably, the subject is avian, swine, bovine or human. Most preferably, the subject is a human.

In the methods of the present invention, the compound or composition is preferably effective against multi-drug resistant clinical bacteria.

In the methods of the present invention, the compound or composition is preferably administered intravenously, parenterally, orally and/or topically.

Another object of the present invention is a method for producing a compound of formula (I) comprising the following steps:
  growing *Xenorhabdus nematophila* strain CNCM I-4530 in a liquid culture medium; and
  purifying a compound according to formula (I):

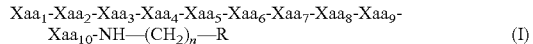

Wherein
$Xaa_1$, $Xaa_2$, $Xaa_3$, $Xaa_5$, $Xaa_7$, $Xaa_8$ and $Xaa_{10}$ are independently selected from the group consisting of lysine, 3-hydroxylysine, 4-hydroxylysine, 5-hydroxylysine, 3,4-dihydroxylysine, 3,5-dihydroxylysine, 4,5-dihydroxylysine, ornithine, 3-hydroxyornithine, 4-hydroxyornithine, 3,4-dihydroxyornithine, 2,4-diaminobutanoic acid, 3-hydroxy-2,4-diaminobutanoic acid, arginine, histidine, serine, and threonine;

$Xaa_4$ is glycine, 3-aminopropanoic acid, or 4-aminobutanoic acid;

$Xaa_6$ is proline, 3-hydroxyproline, 4-hydroxyproline, aziridine-2-carboxylic acid, azetidine-2-carboxylic acid, pipecolic acid, 4-oxaproline, 3-thiaproline, 4-thiaproline, 3,4-dehydroproline, 4-aminoproline, 4-fluoroproline, α-methylproline, or α-allylproline;

$Xaa_9$ is arginine, 2,3-dehydroarginine, citrulline, 2,3-dehydrocitrulline, canavanine, or 2,3-dehydrocanavanine;

n is 2, 3, 4, 5, 6, 7, 8, 9, or 10; and

R is —OH, —NH$_2$, or —COOH.

In one embodiment, the present invention is directed to a method for producing a compound of formula (I), wherein $Xaa_1$ is lysine; $Xaa_2$ and $Xaa_3$ are each 3-hydroxy-2,4-diaminobutanoic acid; $Xaa_4$ is glycine; $Xaa_5$ is ornithine; $Xaa_6$ is proline; $Xaa_7$ is histidine; and $Xaa_9$ is 2,3-dehydroarginine.

In another embodiment, the present invention is directed to a method for producing a compound of formula (I), wherein $Xaa_1$ is lysine; $Xaa_2$ and $Xaa_3$ are each 3-hydroxy-2,4-diaminobutanoic acid; $Xaa_4$ is glycine; $Xaa_5$ is ornithine; $Xaa_6$ is proline; $Xaa_7$ is histidine; $Xaa_8$ is lysine or 5-hydroxylysine; $Xaa_9$ is 2,3-dehydroarginine; and $Xaa_{10}$ is lysine or 5-hydroxylysine.

In another embodiment, the present invention is directed to a method for producing a compound of formula (I), wherein $Xaa_1$ is lysine; $Xaa_2$ and $Xaa_3$ are each 3-hydroxy-2,4-diaminobutanoic acid; $Xaa_4$ is glycine; $Xaa_5$ is ornithine; $Xaa_6$ is proline; $Xaa_7$ is histidine; $Xaa_8$ is lysine or 5-hydroxylysine; $Xaa_9$ is 2,3-dehydroarginine; $Xaa_{10}$ is lysine or 5-hydroxylysine; n is 4; and R is NH$_2$.

In another embodiment, the present invention is directed to a method for producing a compound of formula (I), wherein the compound of formula (I) is (Ia)

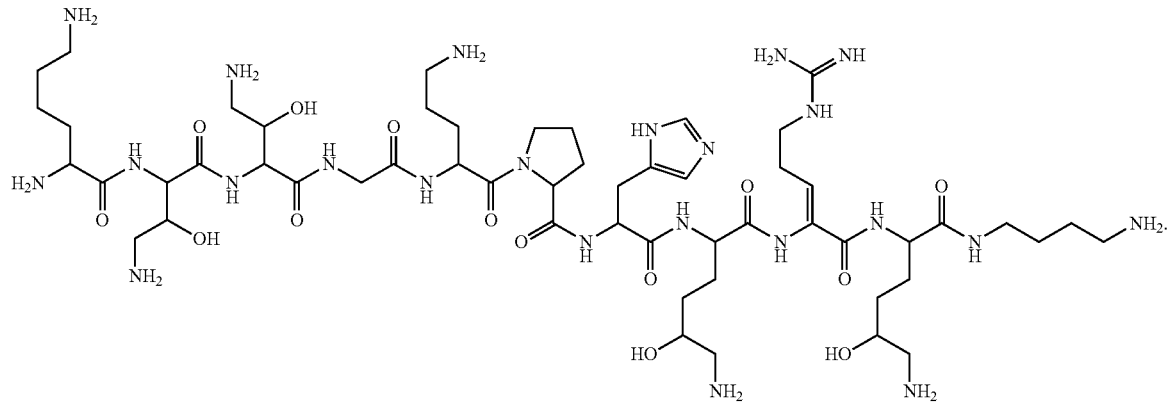

In preferred embodiments, the purifying step comprises cation-exchange chromatography and/or reverse-phase chromatography.

Another object of the present invention is a *Xenorhabdus nematophila* strain deposited at CNCM on 21 Sep. 2011 having the accession number CNCM I-4530.

Another object of the present invention is a culture supernatant from the *Xenorhabdus nematophila* strain CNCM I-4530 having antibiotic activity.

DETAILED DESCRIPTION OF THE INVENTION

Definitions and Abbreviations

Figure 1:
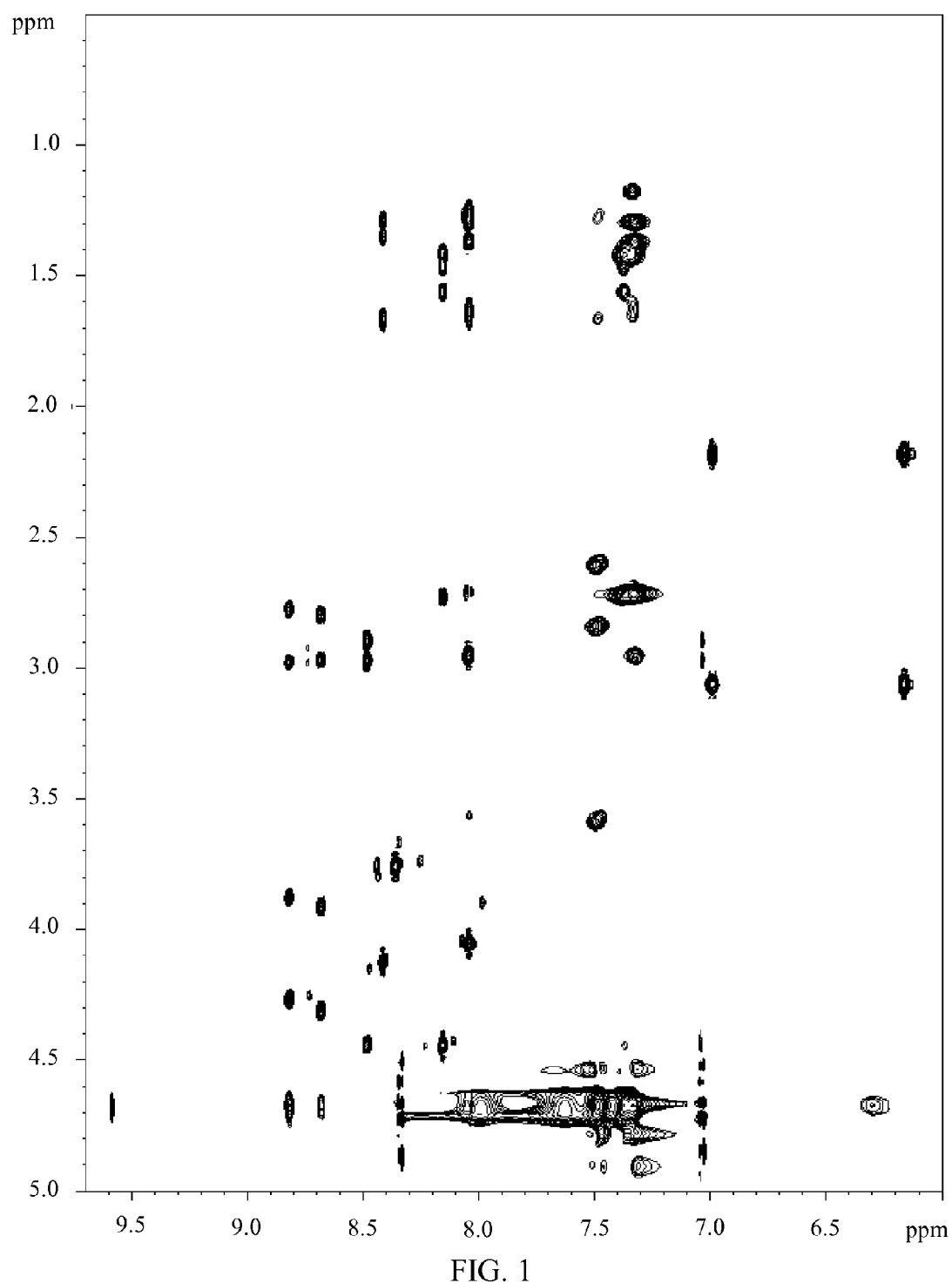
FIG. 1 shows NMR TOCSY spectrum of Odilomycin A

The terms "antibiotic", "antibiotic activity", "antibacterial", "antibacterial activity", "antimicrobial", or "antimicrobial activity" as used herein refer generally to an effect in which a reduction, inhibition or a halt in the growth of a microorganism is achieved. Antibiotic activity may be tested according to any known method such as, for example, a microdilution method.

The term "ODILOMYCIN", "Odilomycin" or "odilomycin" as used herein refers a compound of formula (I). In some embodiments, the compound of formula (I) is a compound of formula (Ia), formula (Ib), and/or formula (Ic). The term is intended to encompass all stereoisomeric forms such as, for example, tautomers, diastereomers (including cis/trans isomers) and enantiomers.

A "pharmaceutical composition" refers to a mixture of one or more of the compounds described herein, or pharmaceutically acceptable salts thereof, with other chemical components, such as physiologically acceptable carriers and excipients. The purpose of a pharmaceutical composition is to facilitate administration of a compound to an organism or subject.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 10 percent up or down (higher or lower).

An "effective amount", "sufficient amount" or "therapeutically effective amount" as used herein is an amount of a compound that is sufficient to effect beneficial or desired therapeutic effect, including clinical results, commensurate with a reasonable benefit/risk ratio, when administered in accordance with a desired treatment regimen. As such, the effective amount may be sufficient, for example, to reduce or ameliorate the severity and/or duration of bacterial infection, afflictions related thereto, or one or more symptoms thereof; prevent the advancement of conditions or symptoms (including prophylactic prevention) related to afflictions related to bacterial infection, afflictions related thereto, or one or more symptoms thereof; or enhance or otherwise improve the prophylactic or therapeutic effect(s) of another therapy. An effective amount also includes the amount of the compound that avoids or substantially attenuates undesirable side effects.

The term "carrier" refers to a diluent, adjuvant, excipient, or vehicle with which a compound is administered. Pharmaceutically acceptable carriers include any and all solvents, dispersion media, coatings and the like that are physiologically compatible. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington's Pharmaceutical Sciences (Alfonso Gennaro ed., Krieger Publishing Company (1997); Remington's: The Science and Practice of Pharmacy, 21$^{st}$ Ed. (Lippincot, Williams & Wilkins (2005); and Modern Pharmaceutics, vol. 121 (Gilbert Banker and Christopher Rhodes, CRC Press (2002).

Abbreviations: ATCC (American Type Culture Collection), CNCM (Collection Nationale de Cultures de Microorganismes), INRA (Institut National de la Recherche Agronomique), MRSA (methicillin-resistant *Staphylococcus aureus*), VRE (vancomycin-resistant enterococci), ESBL (extended spectrum β-lactamase formers), NMR (nuclear magnetic resonance), MS-MS (mass spectroscopy-mass spectroscopy), LC-MS (liquid chromatography-mass spectroscopy), ESI (electrospray ionization), HPLC (high-pressure liquid chromatography), LB (Luria-Bertani medium), NBTA (Nutrient agar (Difco) 31 g/L, bromothymol blue 25 mg/L and 2,3,5-triphenyl tetrazolium chloride 1% 40 mg/L), TFA (trifluoroacetic acid), UV (ultraviolet), MIC (minimal inhibitory concentration), MHB (Mueller-Hinton broth), MBCs (Minimal bactericidal concentrations)

Description

In one aspect, the present invention is related to *Xenorhabdus nematophila* strain 108 deposited at CNCM (Collection Nationale de Cultures de Microorganismes) in the name of INRA (Institut National de la Recherche Agronomique) on 21 Sep. 2011 having the accession number CNCM I-4530.

It has been found that *Xenorhabdus nematophila* strain CNCM I-4530 produces compounds exhibiting antibiotic or antimicrobial activity. When *Xenorhabdus nematophila* strain CNCM I-4530 is grown in a liquid culture medium, antibiotic compounds are secreted into the culture supernatant.

In another aspect, the present invention is related to a culture supernatant from *Xenorhabdus nematophila* strain CNCM I-4530 exhibiting antibiotic or antibacterial activity. For the preparation of a culture supernatant having antibiotic activity *Xenorhabdus nematophila* strain CNCM I-4530 is grown in a liquid culture medium under standard conditions, the bacterial cells are removed and the supernatant is recovered. The bacterial cells may, for example, be removed by centrifugation or filtration.

In yet another aspect, the invention is related to extracts from *Xenorhabdus nematophila* strain CNCM I-4530 showing antibiotic activity. Cell extracts from *Xenorhabdus nematophila* may be prepared according to any appropriate method known to the skilled person.

In some embodiments, the present invention also encompasses culture supernatant and extracts from *Xenorhabdus nematophila* strain CNCM I-4530 for use as medicament.

In some embodiments, the present invention comprises methods of treatment, suppression and/or prevention of bacterial infection comprising administration of extracts from *Xenorhabdus nematophila* strain CNCM I-4530.

In some embodiments, the present invention also encompasses culture supernatant and extracts from *Xenorhabdus nematophila* strain CNCM I-4530 for use as an antibiotic agent.

*Xenorhabdus nematophila* strain CNCM I-4530, culture supernatant from this strain and cell extracts derived from this strain exhibit antibiotic activity against different microorganisms including, for example, human bacterial pathogens.

More particularly, *Xenorhabdus nematophila* strain CNCM I-4530, culture supernatant from this strain and cell extracts derived from this strain exhibit antibiotic activity against *Acinetobacter baumannii, Bacillus subtilis, Burkholderia cepacia, Enterobacter clocae, Enterococcus faecalis, Escherichia coli, Klebsiella pneumoniae, Staphylococcus aureus, Staphylococcus epidermidis, Stenotrophomonas maltophilia, Serratia marescens* and *Pseudomonas aeruginosa*. Preferably, *Xenorhabdus nematophila* strain CNCM I-4530, culture supernatant from this strain and cell extracts derived from this strain exhibit antibiotic activity against *Staphylococcus aureus, Staphylococcus epidermidis, Bacillus subtilis, Klebsiella pneumonia, Klebsiella oxytoca, Acinetobacter baumannii, Enterobacter cloacae, Escherichia coli, Moraxella catarrhalis, Pseudomonas aeruginos* and *Stenotrophomonas maltophilia*.

Exemplary compounds having antibiotic activity as described herein have been purified from the culture supernatant of *Xenorhabdus nematophila* strain CNCM I-4530.

In yet another aspect, the present invention is related to a compound of formula (I):

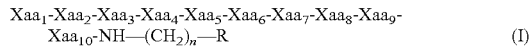

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}NH\text{---}(CH_2)_n\text{---}R \quad (I)$$

wherein $Xaa_1$, $Xaa_2$, $Xaa_3$, $Xaa_5$, $Xaa_7$, $Xaa_8$ and $Xaa_{10}$ are independently selected from the group consisting of lysine, 3-hydroxylysine, 4-hydroxylysine, 5-hydroxylysine, 3,4-dihydroxylysine, 3,5-dihydroxylysine, 4,5-dihydroxylysine, ornithine, 3-hydroxyornithine, 4-hydroxyornithine, 3,4-dihydroxyornithine, 2,4-diaminobutanoic acid, 3-hydroxy-2,4-diaminobutanoic acid, arginine, histidine, serine, and threonine;

$Xaa_4$ is glycine, 3-aminopropanoic acid, or 4-aminobutanoic acid;

$Xaa_6$ is proline, 3-hydroxyproline, 4-hydroxyproline, aziridine-2-carboxylic acid, azetidine-2-carboxylic acid, pipecolic acid, 4-oxaproline, 3-thiaproline, 4-thiaproline, 3,4-dehydroproline, 4-aminoproline, 4-fluoroproline, α-methylproline, or α-allylproline; $Xaa_9$ is arginine, 2,3-dehydroarginine, citrulline, 2,3-dehydrocitrulline, canavanine, or 2,3-dehydrocanavanine;

n is 2, 3, 4, 5, 6, 7, 8, 9, or 10; and

R is —OH, —$NH_2$, or —COOH.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, and $Xaa_9$ is 2,3-dehydroarginine.

In some embodiments, $Xaa_1$ is lysine.

In some embodiments, $Xaa_2$ is 3-hydroxy-2,4-diaminobutanoic acid.

In some embodiments, $Xaa_3$ is 3-hydroxy-2,4-diaminobutanoic acid.

In some embodiments, $Xaa_4$ is glycine.

In some embodiments, $Xaa_5$ is ornithine.

In some embodiments, $Xaa_6$ is proline.

In some embodiments, $Xaa_7$ is histidine.

In some embodiments, $Xaa_8$ is lysine or 5-hydroxylysine.

In some embodiments, $Xaa_9$ is 2,3-dehydroarginine.

In some embodiments, $Xaa_{10}$ is lysine or 5-hydroxylysine.

In some embodiments, n=4.

In some embodiments, R is —$NH_2$.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, $Xaa_8$ is lysine or 5-hydroxylysine, $Xaa_9$ is 2,3-dehydroarginine, and $Xaa_{10}$ is lysine or 5-hydroxylysine.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, $Xaa_8$ is lysine or 5-hydroxylysine, $Xaa_9$ is 2,3-dehydroarginine, $Xaa_{10}$ is lysine or 5-hydroxylysine, n is 4 and R is $NH_2$.

The configuration at the α-carbon atoms in the amino acid residues may be "D" or "L", and may be independent of the configurations of other amino acid residues in the compounds of formula (I). Thus, in some embodiments, $Xaa_1$, $Xaa_2$, $Xaa_3$, $Xaa_4$, $Xaa_5$, $Xaa_6$, $Xaa_7$, $Xaa_8$, and $Xaa_{10}$ each have the "L" configuration at the α-carbon of the amino acid residue. In some embodiments, one or more of $Xaa_1$, $Xaa_2$, $Xaa_3$, $Xaa_4$, $Xaa_5$, $Xaa_6$, $Xaa_7$, $Xaa_8$, and $Xaa_{10}$ have the "D" configuration at the α-carbon of the amino acid residue.

The configuration at the hydroxyl groups in the amino acid side chains may be "R" or "S", and may be independent of the configurations of other hydroxyl groups in the compounds of formula (I). Thus, in some embodiments, one or more hydroxyl groups have the "R" configuration. In some embodiments, one or more hydroxyl groups have the "S" configuration. In some embodiments, each of the hydroxyl groups have the "R" configuration. In some embodiments, each of the hydroxyl groups have the "S" configuration.

In some embodiments, the compound of formula (I) is the compound of formula (Ia):

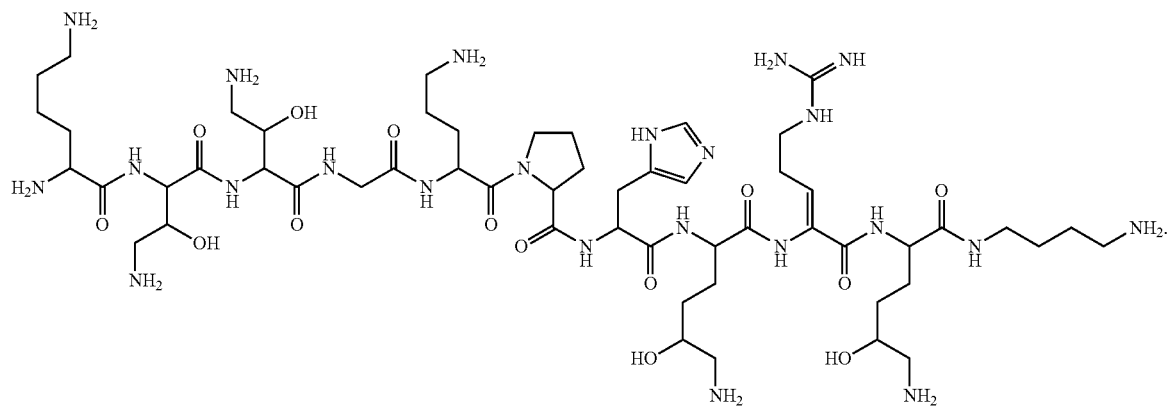

(Ia)

The compound of formula (Ia) is also defined as Lys-(3-hydroxy-2,4-diaminobutanoic acid)-(3-hydroxy-2,4-diaminobutanoic acid)-Gly-Ornithine-Pro-His-(5-hydroxylysine)-(2,3-dehydroarginine)-(5-hydroxylysine)-(1,4-diaminobutane).

The term "Odilomycin A" refers to the compound of formula (Ia).

In some embodiments, the compound of formula (I) is the compound of formula (Ib):

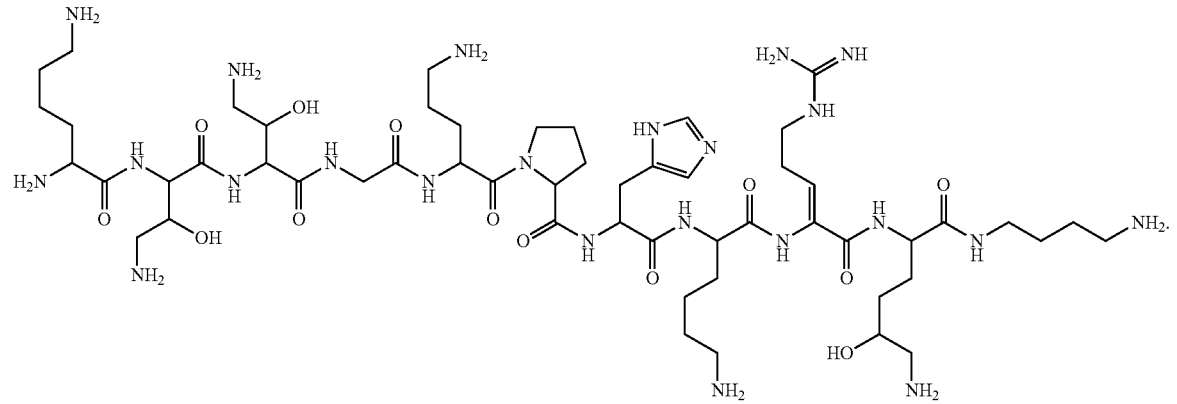

(Ib)

The compound of formula (IIb) is also defined as Lys-(3-hydroxy-2,4-diaminobutanoic acid)-(3-hydroxy-2,4-diaminobutanoic acid)-Gly-Ornithine-Pro-His-Lys-(2,3-dehydroarginine)-(5-hydroxylysine)-(1,4-diaminobutane).

The term "Odilomycin B" refers to the compound of formula (Ib).

In some embodiments, the compound of formula (I) is the compound of formula (Ic):

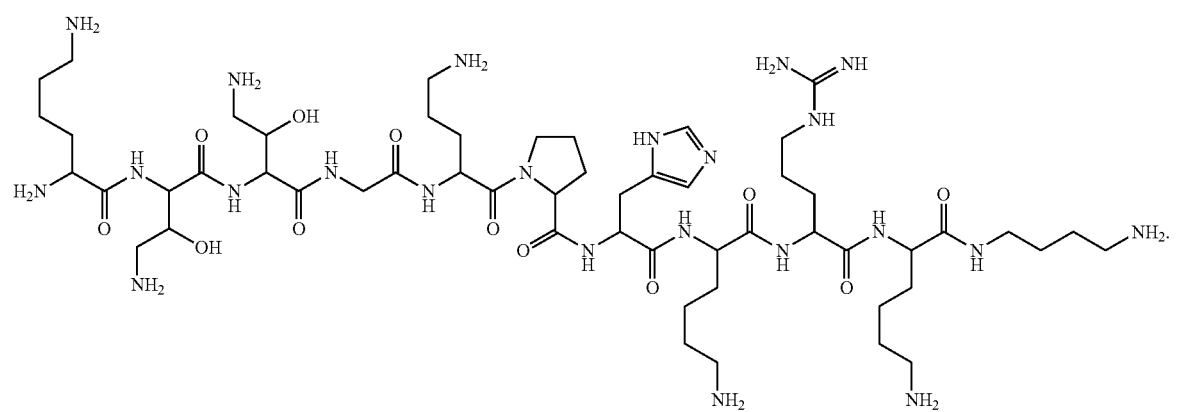

(Ic)

The compound of formula (Ic) is also defined as Lys-(3-hydroxy-2,4-diaminobutanoic acid)-(3-hydroxy-2,4-diaminobutanoic acid)-Gly-Ornithine-Pro-His-Lys-(2,3-dehydroarginine)-Lys-(1,4-diaminobutane).

The term "Odilomycin C" refers to the compound of formula (Ic).

In some embodiments, Odilomycins do not include the compounds of formulas (Ia), (Ib), and (Ic).

In some embodiments, the Odilomycins are isolated.

In some embodiments, the Odilomycins are greater than about 50% pure. In some embodiments, the Odilomycins are greater than about 60% pure. In some embodiments, the Odilomycins are greater than about 70% pure. In some embodiments, the Odilomycins are greater than about 80% pure. In some embodiments, the Odilomycins are greater than about 85% pure. In some embodiments, the Odilomycins are greater than about 90% pure. In some embodiments, the Odilomycins are greater than about 95% pure. In some embodiments, the Odilomycins are greater than about 98% pure. In some embodiments, the Odilomycins are greater than about 99% pure. In some embodiments, any stated purity values can form a lower and/or upper endpoint of a purity range as appropriate or where any of the lower limits can be combined with any of the upper limits.

In some embodiments, Odilomycins and/or compositions comprising the same are useful as a medicament, an antibiotic agent, an antimicrobial agent, or in the treatment of microbial disease, in particular of bacterial infection caused, for example, by pathogenic bacteria.

In some embodiments, Odilomycins and/or compositions comprising the same are useful in the treatment of a bacterial infection, for example in the treatment of a hospital-acquired infection or a nosocomial bacterial infection.

In some embodiments, the present invention provides a method for treating a subject suffering from hospital-acquired bacterial infection comprising administering to said subject an effective amount of a compound of formula (I).

In some embodiments, the present invention provides a method for treating a subject suffering from nosocomial bacterial infection comprising administering to said subject an effective amount of a compound of formula (I).

In one aspect, the invention is also related to the use of compounds of formula (I) for the manufacture of a medicament for treatment of microbial infection or microbial disease.

In another aspect, the invention is also related to the use of compounds of formula (I) for the manufacture of an antibiotic composition.

In yet another aspect, the present invention is also directed to methods of treatment comprising administration of a compound of formula (I), or pharmaceutical compositions comprising a compound of formula (I), to a subject in need thereof. The Odilomycins and/or compositions comprising the same may be useful, for example, in treatment, suppression, and/or prevention of bacterial infection and/or disease.

In some embodiments, the invention provides a method of treating, preventing, and/or suppressing bacterial infection comprising administering to a subject in need thereof a therapeutically effective amount of a compound of formula (I) or a composition comprising a compound of formula (I).

In some embodiments, the present invention provides a method for treating a subject suffering from a bacterial infection comprising administering to said subject a compound of formula (I).

In some embodiments, the present invention provides a method for suppressing a bacterial infection in a subject comprising administering to the subject a compound of formula (I).

In still some embodiments, the present invention provides a method for treating a subject suffering from multi-drug resistant bacterial infection comprising administering to said subject an effective amount of a compound of formula (I).

In some embodiments, methods of the present invention provide for inhibition of bacteria, or infection related thereto, that are resistant to other drugs or antibiotics. In some embodiments, the methods provide for treatment, suppression, and/or prevention of infection from multi-drug resistant bacteria.

In some embodiments, the bacterial infection is multi-drug resistant. In some embodiments, the bacterial strain is hospital-acquired. In some embodiments, the bacterial strain is nosocomial.

In some embodiments, the bacterial infection comprises infection from Gram-negative bacteria. In some embodiments, the bacterial infection comprises infection from Gram-positive bacteria. In some embodiments, the bacterial infection comprises infection by more than one bacterial strain.

In some embodiments, the bacterial or microbial infection is an infection caused in whole or in part by bacteria of the *Achromobacter, Actinobacillus, Actinomyces, Acinetobacter, Aeromonas, Anaplasma, Bacillus, Bacteroides, Bartonella, Bdellovibrio, Bifidobacterium, Bordetella, Borrelia, Brucella, Burkholderia, Campylobacter, Capnocytophaga, Cardiobacterium, Chlamydia, Chlamydophila, Chromobacterium, Citrobacter, Clostridium, Corynebacterium, Coxiella, Ehrlichia, Enterobacter, Enterococcus, Erysipelothrix, Escherichia, Francisella, Fusobacterium, Haemophilus, Helicobacter, Hemobartonella, Klebsiella, Lactobacillus, Legionella, Leptospira, Listeria, Mannheimia, Moraxella, Morganella, Mycobacterium, Mycoplasma, Neisseria, Neorickettsia, Nocardia, Pasteurella, Peptostreptococcus, Photorhabdus, Porphyromonas, Prevotella, Propionibacterium, Proteus, Pseudomonas, Rickettsia, Salmonella, Serratia, Shigella, Sphaerophorus, Spirillum, Staphylococcus, Stenotrophomonas, Streptobacillus, Streptococcus, Treponema, Tropheryma, Ureaplasma, Vibrio,* or *Yersinia* families.

In some embodiments, the bacterial or microbial infection is an infection caused in whole or in part by *Acinetobacter baumannii, Bacillus subtilis, Burkholderia cepacia, Enterobacter clocae, Enterococcus faecalis, Escherichia coli, Klebsiella pneumoniae, Staphylococcus aureus, Staphylococcus epidermidis, Stenotrophomonas maltophilia, Serratia marescens* or *Pseudomonas aeruginosa*. Preferably, *Xenorhabdus nematophila* strain CNCM I-4530, culture supernatant from this strain and cell extracts derived from this strain exhibit antibiotic activity against *Staphylococcus aureus, Staphylococcus epidermidis, Bacillus subtilis, Klebsiella pneumonia, Klebsiella oxytoca, Acinetobacter baumannii, Enterobacter cloacae, Escherichia coli, Moraxella catarrhalis, Pseudomonas aeruginos* and *Stenotrophomonas maltophilia*.

In some embodiments, the disclosure provides for the use of pharmaceutical compositions and/or medicaments comprised of the compound of formula (I) in a method of treating a bacterial infection, and/or disease state, and/or condition caused by or related to such bacterial infection.

In some embodiments, the methods comprise administering to the subject an effective amount of a compound of formula (I) alone or in combination with a second antibiotic compound, or a composition comprising a compound of formula (I) alone or in combination with a second antibiotic compound and a pharmaceutically acceptable carrier. The pharmaceutically acceptable carriers are well-known to those skilled in the art, and include, for example, adjuvants, diluents, excipients, fillers, lubricants and vehicles. Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols.

In some embodiments, the method of treatment, prevention and/or suppression of a condition related to bacterial infection comprises the steps of: (i) identifying a subject in need of such treatment; (ii) providing a compound of formula (I) alone or in combination with a second antibiotic compound, or a composition comprising a compound of formula (I) alone or in combination with a second antibiotic compound and a pharmaceutically acceptable carrier; and (iii) administering said compound(s) or composition in a therapeutically effective amount to treat, prevent and/or suppress bacterial infection in a subject in need of such treatment.

In some embodiments, the methods comprise administering to the subject an effective amount of a compound of formula (I); or a composition comprising a compound of formula (I) and a pharmaceutically acceptable carrier.

In some embodiments, the method of treatment, prevention and/or suppression of a condition related to bacterial infection comprises the steps of: (i) identifying a subject in need of such treatment; (ii) providing a compound of formula (I) or a composition comprising a compound of formula (I) a pharmaceutically acceptable carrier; and (iii) administering said compound or composition in a therapeutically effective amount to treat, prevent and/or suppress the disease state or condition related to bacterial infection in a subject in need of such treatment.

In some embodiments, treatment refers generally to treatment and therapy, whether of a human or an animal (e.g., in veterinary applications), in which some desired therapeutic effect is achieved, for example, the inhibition of the progress of the condition. Treatment may also include, but is not limited to, a reduction in the rate of progress, a halt in the rate of progress, amelioration of the condition, cure of the condition a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. In some embodiments, treatment can also mean prolonging survival as compared to expected survival if not receiving treatment. In some embodiments, treatment as a prophylactic measure (i.e., prophylaxis) is also included. For example, use with subjects who have not yet developed the condition, but who are at risk of developing the condition, is encompassed by the term "treatment."

In some embodiments, treatment comprises combination treatments and therapies, in which two or more treatments or therapies are combined, for example, sequentially or simultaneously. For example, the active agents of the present invention may also be used in further combination therapies, e.g., in conjunction with other agents, for example, other antimicrobial or antibiotic agents, etc.

The subjects are in vitro and in vivo systems, including, for example, isolated or cultured cells or tissues, non-cellular in vitro assay systems and animals (e.g., an amphibian, a bird, a fish, a mammal, a marsupial, a human, a domestic animal such as, for example, a cat, dog, monkey, mouse or rat; or a commercial animal such as, for example, a horse, bovine (such as a cow), turkey, chicken or pig)).

In some embodiments, the subject is a mammal. In some embodiments, the subject is avian, swine, a bovine or a human. In some embodiments, the subject is a human. In some embodiments, the subject is avian. In some embodiments, the subject is a swine or pig. In some embodiments, the subject is a turkey or chicken.

In addition, the compositions or methods may further comprise one or more additional antibacterial or antibiotic compounds in combination with a compound of formula (I) alone. Examples of such compounds include, but are not limited to, daptomycin, oxacillin, piperacillin/tazobactam, ticaricillin/clavulanic acid, amoxicillin/clavulanic acid, erythromycin, cefepim, clindamycin, imipenem, gentamicin, ciprofloxacin, aztreonam, vancomycin, linezolid, rifampicin, kanamycin, ampicillin, tetracycline, and the like.

In some embodiments, the additional (or second) antibiotic is an aminoglycoside antibiotic. Aminoglycoside antibiotics are antibiotic compounds in which a portion of a molecule contains an amino-modified sugar. Examples of aminoglycoside antibiotics include, but are not limited to amikacin, apramycin, arbekacin, astromicin, bekanamycin, capreomycin, dibekacin, dihydrostreptomycin, elsamitrucin, G418, gentamicin, hygromycin B, isepamicin, kanamycin, kasugamycin, micronomicin, neomycin, netilmicin, paromomycin sulfate, ribostamycin, sisomicin, streptoduocin, streptomycin, tobramycin and verdamicin.

Thus, in some embodiments the methods and/or compositions further comprise one or more additional antibacterial compounds in combination with a compound of formula (I). In some embodiments, the additional antibacterial compound is selected from the group consisting of daptomycin, oxacillin, piperacillin/tazobactam, ticaricillin.clavulanic acid, amoxicillin/clavulanic acid, erythromycin, cefepim, clindamycin, imipenem, gentamicin, ciprofloxacin, aztreonam, vancomycin, linezolid, rifampicin, kanamycin, ampicillin, and tetracycline. In some embodiments, the additional antibacterial is kanamycin. In some embodiments, the additional antibiotic is an aminoglycoside antibiotic.

In some embodiments, the present invention provides a method for treating, suppressing and/or preventing bacterial infection by combined use of the compound of formula (I) and a second antibiotic compound in subjects wherein the use of either the compound of formula (I) or the second antibiotic compound alone does not provide the desired therapeutic effect. Surprisingly, it has been found that when other antibiotic compounds are used together with a compound of formula (I), statistically significant increases in antibiotic effects are observed. In some embodiments, there is a synergistic effect between a second antibiotic compound, such as kanamycin, and the compound of formula (I). Thus, in some embodiments, kanamycin and the compound of formula (I) are administered in amounts that exhibit synergistic lowering of bacterial levels. In some embodiments, a kanamycin and the compound of formula (I) are administered in amounts that exhibit synergistic treatment, suppression and/or prevention of bacterial infection.

Another aspect of the present invention is a pharmaceutical composition comprising an effective amount of a compound of formula (I). In some embodiments, $Xaa_1$ is lysine.

In some embodiments, $Xaa_2$ is 3-hydroxy-2,4-diaminobutanoic acid.

In some embodiments, $Xaa_3$ is 3-hydroxy-2,4-diaminobutanoic acid.

In some embodiments, $Xaa_4$ is glycine.
In some embodiments, $Xaa_5$ is ornithine.
In some embodiments, $Xaa_6$ is proline.
In some embodiments, $Xaa_7$ is histidine.
In some embodiments, $Xaa_8$ is lysine or 5-hydroxylysine.
In some embodiments, $Xaa_9$ is 2,3-dehydroarginine.
In some embodiments, $Xaa_{10}$ is lysine or 5-hydroxylysine.
In some embodiments, n=4.
In some embodiments, R is —$NH_2$.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, and $Xaa_9$ is 2,3-dehydroarginine.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, $Xaa_8$ is lysine or 5-hydroxylysine, $Xaa_9$ is 2,3-dehydroarginine, and $Xaa_{10}$ is lysine or 5-hydroxylysine.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, $Xaa_8$ is lysine or 5-hydroxylysine, $Xaa_9$ is 2,3-dehydroarginine, $Xaa_{10}$ is lysine or 5-hydroxylysine, n is 4 and R is $NH_2$.

In some embodiments, the present invention provides for the use of pharmaceutical compositions and/or medicaments comprised of a compound of formula (I), in a method of treating, suppressing and/or preventing a disease state, and/or condition caused by or related to bacterial infection.

In some embodiments, the method of treatment comprises the steps of: (i) identifying a subject in need of such treatment; (ii) providing a compound of formula (I); and (iii) administering said compound of formula (I) in a therapeutically effective amount to treat, suppress and/or prevent the disease state or condition in a subject in need of such treatment.

In some embodiments, the method of treatment comprises the steps of: (i) identifying a subject in need of such treatment; (ii) providing a composition comprising a compound of formula (I); and (iii) administering said composition in a therapeutically effective amount to treat, suppress and/or prevent the disease state or condition in a subject in need of such treatment.

In some embodiments, the Odilomycins are formulated into pharmaceutical compositions for administration to subjects in a biologically compatible form suitable for administration in vivo. According to another aspect, the present invention provides a pharmaceutical composition comprising a compound of formula (I) in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations.

When administered to a subject, the compound of the present invention and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical compositions or formulations of the present invention are prepared by methods well-known in the pharmaceutical arts. For example, the compounds of formula (I) are brought into association with a carrier and/or diluent, as a suspension or solution. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, Odilomycins or compositions comprising same are administered to a subject by known procedures including, without limitation, oral administration, sublingual or buccal administration, parenteral administration, topical administration, transdermal administration, via inhalation or intranasally, vaginally, rectally, and intramuscularly. The compounds or compositions are administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous or sublingual injection, or by way of catheter.

In some embodiments, the compound and/or composition is administered orally. In some embodiments, the compound and/or composition is administered subcutaneously. In some embodiments, the compound and/or composition is administered intravenously. In some embodiments, the compound and/or composition is administered intramuscularly. In some embodiments, the compound and/or composition is administered topically. In some embodiments, the compound and/or composition is administered parenterally.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In some embodiments, the pharmaceutical compositions for oral use comprise an Odilomycin together with the usual excipients as diluting agents such as mannitol, lactose and sorbitol; binding agents such as starches, gelatins, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; and other coloring, flavoring and sweetening agents.

In some embodiments, the compositions comprise an Odilomycin with carriers or excipients suitable for topical administration. Any topical preparation may be used in the present invention, for instance ointments, pomades, creams, gels and lotions. Exemplary compositions for topical administration according to the invention include ointments, pomades, creams, gels, and lotions.

The doses of an Odilomycin depend on the desired effect, the duration of the treatment and the route of administration used.

In some embodiments, the pharmaceutical compositions according to the present invention are for use as an antimicrobial agent, for use as antibiotics or for use in the treatment of microbial disease, in particular of microbial disease caused by bacteria.

The pharmaceutical compositions of the present invention are preferably for use in the treatment of bacterial infection and in particular for use in the treatment of hospital-acquired infections or nosocomial bacterial infections.

The Odilomycins may be combined with other active compounds exhibiting an antimicrobial/antibiotic activity. The pharmaceutical compositions encompassed by the present invention may also comprise a further therapeutic agent for the treatment of bacterial disease or bacterial infection.

In some embodiments, the methods comprise administration of a therapeutically effective dosage of an Odilomycin. The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens. The precise dose to be employed in the compositions will also depend on the route of administration, and should be decided according to the judgment of the practitioner and each patient's circumstances.

Any of the compounds and/or compositions may be provided in a kit comprising the compounds and/or compositions. Thus, in some embodiments, the compound and/or composition is provided in a kit.

Another aspect of the present invention is a method for producing a compound of formula (I) comprising the following steps:

a) growing *Xenorhabdus nematophila* strain CNCM I-4530 in a liquid culture medium; and
b) purifying a compound of formula (I).

In some embodiments of the compound of formula (I), $Xaa_1$ is lysine. In some embodiments, $Xaa_2$ is 3-hydroxy-2,4-diaminobutanoic acid. In some embodiments, $Xaa_3$ is 3-hydroxy-2,4-diaminobutanoic acid. In some embodiments, $Xaa_4$ is glycine. In some embodiments, $Xaa_5$ is ornithine. In some embodiments, $Xaa_6$ is proline. In some embodiments, $Xaa_7$ is histidine. In some embodiments, $Xaa_8$ is lysine or 5-hydroxylysine. In some embodiments, $Xaa_9$ is 2,3-dehydroarginine. In some embodiments, $Xaa_{10}$ is lysine or 5-hydroxylysine. In some embodiments, n=4. In some embodiments, R is —$NH_2$.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, $Xaa_8$ is lysine or 5-hydroxylysine, $Xaa_9$ is 2,3-dehydroarginine, and $Xaa_{10}$ is lysine or 5-hydroxylysine.

In some embodiments, $Xaa_1$ is lysine, $Xaa_2$ and $Xaa_3$ are each 3-hydroxy-2,4-diaminobutanoic acid, $Xaa_4$ is glycine, $Xaa_5$ is ornithine, $Xaa_6$ is proline, $Xaa_7$ is histidine, $Xaa_8$ is lysine or 5-hydroxylysine, $Xaa_9$ is 2,3-dehydroarginine, $Xaa_{10}$ is lysine or 5-hydroxylysine, n is 4 and R is $NH_2$.

In some embodiments, the compound of formula (I) is the compound of formula (Ia).

In some embodiments, the compound of formula (I) is the compound of formula (Ib).

In some embodiments, the compound of formula (I) is the compound of formula (Ic).

The Odilomycins can be purified from the *Xenorhabdus nematophila* cells of the present invention. Advantageously, the compounds may be purified from the culture supernatant after removal of the *Xenorhabdus nematophila* cells. For the preparation of a culture supernatant having antibacterial activity *Xenorhabdus nematophila* strain CNCM I-4530 is grown in a liquid culture medium under standard conditions, the bacterial cells are removed and the supernatant is recovered. The bacterial cells may for example be removed by centrifugation or filtration.

Further purification of Odilomycins may be carried out by any known method including cation-exchange chromatography, reversed-phase chromatography and/or reverse phase HPLC.

In some embodiments, Odilomycins are purified from the culture supernatant of *Xenorhabdus nematophila* strain CNCM I-4530 by successive cation-exchange chromatography, reversed-phase chromatography and reverse phase HPLC.

Odilomycins can also be synthesized according to standard techniques in the art including, but not limited to, solution phase organic synthesis and solid-phase organic synthesis. In some embodiments, solid-phase organic synthesis comprises synthesis via peptide synthesizer machinery. Such embodiments and execution thereof are well within the scope of the ordinarily skilled artisan. Exemplary synthetic methods are described in Bodanzky, et al. "The Practice of Peptide Synthesis," Springer-Verlag (1994).

Those skilled in the art will recognize, or able to ascertain using no more than routine experimentation, many equivalents to the specific embodiments of the invention described herein. Such equivalents are intended to be within the scope of the present invention.

It will further be recognized that any or all of the combinations, embodiments and aspects of the invention may be combined in any fashion to provide other combinations, embodiments and aspects within the scope of the invention unless otherwise not possible.

The invention is further described by the following non-limiting Examples.

EXAMPLES

Example 1

Production and Fermentation

Producing Organism

*Xenorhabdus nematophila* CNCM I-4530 ('Diversité, genomes et interactions microorganisms-insectes' collection) was grown on Luria-Bertani medium (LB, composed of bactotryptone 10 g/L, yeast extract 5 g/L and NaCl 10 g/L) for liquid culture and on LB-agar for solid cultures. The phase status (I or II) of this strain was determined by culturing on NBTA (Nutrient agar (Difco) 31 g/L, bromothymol blue 25 mg/L and 2,3,5-triphenyl tetrazolium chloride 1% 40 mg/L) and measuring antibacterial activity against *Micrococcus luteus*. *Xenorhabdus* exhibit two colony forms or variants when cultured in vitro. Modifications of the outer membrane induce differential adsorption of dyes by variants. Phase I variants absorb dyes and are blue on NBTA plates, while phase II colonies are red. Phases I and II of strains are indicated as suffixes (/1 and /2, respectively) attached to strain designations. This strain was maintained at 15° C. on NBTA medium.

Fermentation

*Xenorhabdus nematophila* CNCM I-4530 was cultivated for 72 h, at 28° C. with shaking in a 2 L Erlenmeyer flask containing 500 mL of medium broth composed of bactopeptone 15 g/L, $MgSO_4.7H_2O$ 2 g/L and glucose 2 g/L. The culture was inoculated with 0.1% (v/v) of a 24 h pre-culture in the same medium. The antibiotic production was monitored by analytical HPLC.

Example 2

Isolation

Bacterial cells were removed by low-speed centrifugation (6000×g, 10 min at 4° C.) and supernatant was sterilized onto 0.22 μm pore size filter. Supernatant was added (1:1; v/v) to a 0.1 M NaCl-0.02 M Tris buffer (pH 7), and subjected to cation-exchange chromatography on a Sep Pack CarboxyMethyl cartridge (Accell Plus CM, Waters). Unbound material was removed by washes with a 0.1 M NaCl-0.02 M Tris buffer (pH 7) and the antibiotic actives eluted with 1 M NaCl-0.02 M Tris buffer (pH 7). This eluate was acidified with 0.1% (v/v) trifluoroacetic acid (TFA) and was then subjected to reverse-phase chromatography on a Sep Pack C18 cartridge (Sep-Pak Plus C18, Waters). Unbound material was removed by washing with $H_2O$-TFA 0.1% and the antibiotic pool was eluted with acetonitrile. The eluate was freeze-dried then resuspended in water (1:5; v/v). Pure compounds were isolated from the crude extract by reverse phase HPLC using a C18 column (Waters; Symmetry Symmetry C18; 5 μm; 4.6×150 mm), a linear gradient of $H_2O$/0.1% TFA-acetonitrile starting from 0% to 30% in 30 min, a flow rate of 1 mL/min and an UV detection from 200 to 400 nm, yielding Odilomycins with the following HPLC-retention times: Odilomycin A 14.16 min (purity: 98% UV), Odilomycin B 14.44 min (purity: 95% UV) and Odilomycin C 14.6 min (purity: 94% UV).

Example 3

Characterization and Physicochemical Properties

NMR and MS Analysis

The purified compound was analyzed by Mass Spectroscopy and NMR to determine its chemical structure.

The NMR study was carried out on a Bruker Avance spectrometer operating at 700 MHz equipped with a cryoprobe. The sample (10 mM) was solubilized in water (95/5 H₂O/D₂O v/v) and pH was set to 3.5 with hydrochloric acid. All data were recorded at 280° K. Protons chemical shifts are expressed with respect to sodium 4,4-dimethyl-silapentane-1-sulfonate, according to IUPAC recommendations. Double-quantum filtered-correlated spectroscopy (DQF-COSY), z-filtered total-correlated spectroscopy (z-TOCSY) and nuclear Overhauser effect spectroscopy (NOESY) spectra were acquired in the phase-sensitive mode, using the States-TPPI method (Marion D. Et al, *J. Magn. Reson.* 85, 393-399 (1989)). z-TOCSY spectra were obtained with a mixing time of 80 ms and NOESY spectra with mixing times of 220 ms. The $^1$H—$^{13}$C HSQC and $^1$H—$^{13}$C HSQC-TOCSY experiments were carried out with the same sample. The water resonance set at the carrier frequency was suppressed by the WATERGATE method (Piotto M. Et al. *J. Biomol. NMR* 2, 661-665 (1992)). All data were processed with the XWIN-NMR software. The non-classical residues were identified from the analysis of the homo- and hetero-nuclear data. The sequential assignment was achieved using the general strategy described by Wüthrich (Wuthrich K. *NMR of Proteins and Nucleic Acids*, John Wiley & Sons, New York (1986)).

LC-MS was first performed in order to obtain the m/z value of the protonated molecules of all Odilomycin derivatives. MS-MS fragmentation was then carried out on Odilomycin A, B and C. ESI-LC-MS data were obtained in the positive mode on a Waters alliance LC-MS system (Waters ZQ mass detector, Waters photodiode array detector 2696, Waters alliance HPLC systems 2790). The HPLC column used was a C18 column (Waters Symmetry C18 5 µm 4.6×150 mm) maintained at 35° C. Solvents were (A) water+0.1% TFA, (B) acetonitrile+0.1% TFA, and the flow rate was 1 mL/min. The mobile phase composition was 100% A at 0 min, ramped to 30% B at 30 min. Samples were dissolved in solvent A (100 µL). Sample injection volume was 10 µL. UV-Visible detection was by absorbance at 200-400 nm. Solvent flow to the MS was diverted to waste for the first 5 min to minimise salt build-up. MS-MS fragmentation data were obtained on a Waters Micromass Q-T of micro mass spectrometer.

Physico-Chemical Properties of Odilomycins

Three compounds referred as Odilomycin A, B, and C were isolated, purified to homogeneity as a white powder and characterized by mass spectrometry. ESI-MS experiments revealed the molecular weights of different Odilomycins.

Odilomycin A: White powder; UV: $\lambda_{max}$(MeOH)=214 nm; ESI-MS (m/z): 1297 [M+H]$^+$;

Odilomycin B: White powder; UV: $\lambda_{max}$(MeOH)=214 nm; ESI-MS (m/z): 1281 [M+H]$^+$;

Odilomycin C: White powder; UV: $\lambda_{max}$(MeOH)=214 nm; ESI-MS (m/z): 1265 [M+H]$^+$.

Chemical Structure Elucidation

The chemical structure of Odilomycin A was established from the combined analysis of NMR and mass spectrometry data.

Figure 2:
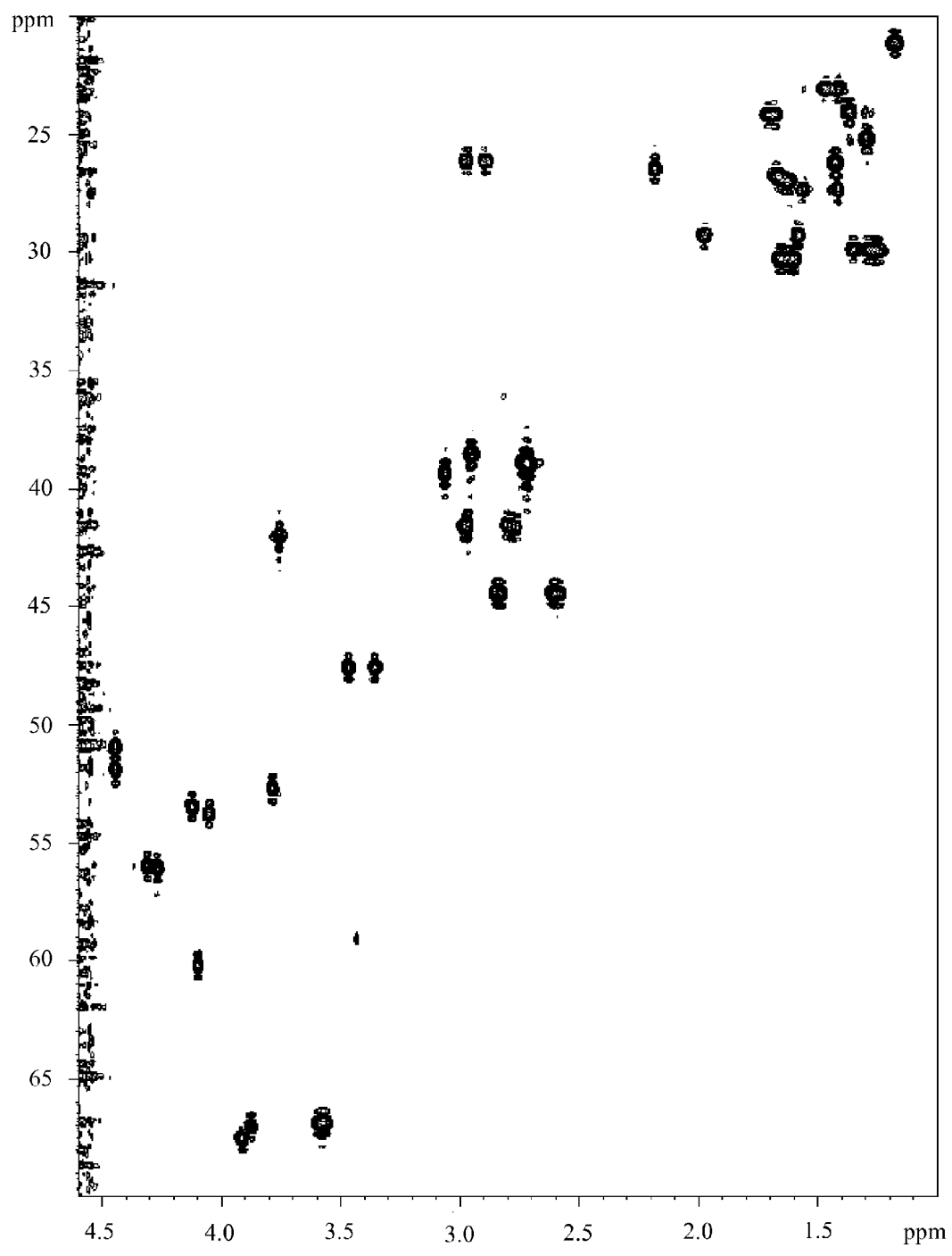
FIG. 2 shows NMR HSQC spectrum of Odilomycin A

NMR data were obtained in water and a set of experiments including DQF-COSY, TOCSY, NOESY, $^1$H—$^{13}$C HSQC and $^1$H—$^{13}$C HSQC-TOCSY experiments were recorded (FIGS. 1 and 2). The 1D spectrum revealed features of a peptidic compound with at least 6 amide signals spanning the 8.9-7.0 ppm chemical shift area, alpha proton signals in the 4.8-3.7 ppm area, and beta proton signals in the 3.7-1.1 ppm area. No methyl signal was observed in the high field area indicating the absence of Ala, Thr, Leu, Val and Ile residues. In contrast, signals including the 9.60 ppm singlet and the 6.17 ppm triplet were observed suggesting the presence of non-classical residues. In addition with homonuclear data, the $^1$H—$^{13}$C heteronuclear data were particularly helpful to characterize the spin systems of the non-classical residues.

The combined analysis of all these data allowed identification of 11 spin systems including 4 types of non-classical residues: an α,γ-diamino β-hydroxy butyric acid (Dab (βOH)), an δ-hydroxy lysine (Dhl), an α,β-dehydro arginine (Dha) and, an α,δ-diamino butane (Dbt). Neither the configuration of the asymmetric carbons of these non-classical residues, nor that of the classical residues was determined. The strong intensity of the Orn$^5$H$_\alpha$-Pro$^6$H$_{\delta\delta'}$ NOE suggests that the Orn$^5$-Pro$^6$ amide bond adopts the trans conformation. By using sequential NOEs, the sequence of this pseudopeptide was identified as following:

Lys$^1$-Dab(βOH)$^2$-Dab(βOH)$^3$-Gly$^4$-Orn$^5$-Pro$^6$-His$^7$-Dhl$^8$-Dha$^9$-Dhl$^{10}$-Dbt$^{11}$

NMR data are reported in Table 1 (Odilomycin A), Table 2 (Odilomycin B), and Table 3 (Odilomycin C).

This sequence is in full agreement with the molecular weight of 1297 Da measured by Mass Spectroscopy data and the non-classical residues confirmed by MS/MS fragmentation data.

TABLE 1

Chemical shifts of Odilomycin A (water, 280K)

| Spin system | Group | $^1$H (ppm) | $^{13}$C (ppm) |
|---|---|---|---|
| Lys$^1$ | HN | — | — |
|  | C$_\alpha$H | 3.8 | 53.0 |
|  | C$_\beta$H$_2$ | 1.66/1.62 | 30.4 |
|  | C$_\gamma$H$_2$ | 1.2 | 21.1 |
|  | C$_\delta$H$_2$ | 1.45 | 26.3 |
|  | C$_\epsilon$H$_2$ | 2.78 | 39.0 |
| Hydroxy Diamino | HN | 8.83 | — |
| butyric acid$^2$ | C$_\alpha$H | 4.28 | 56.3 |
| Dab(βOH)$^2$ | C$_\beta$H-OH | 3.89 | 67.4 |
|  | C$_\gamma$H$_2$ | 2.99/2.79 | 41.9 |
|  | NH$_2$ | — | — |
| Hydroxy Diamino | HN | 8.63 | — |
| butyric acid$^3$ | C$_\alpha$H | 4.33 | 56.3 |
| Dab(βOH)$^3$ | C$_\beta$H-OH | 3.93 | 67.7 |
|  | C$_\gamma$H$_2$ | 2.98/2.80 | 41.5 |
|  | NH$_2$ | — | — |
| Gly$^4$ | HN | 8.37 | — |
|  | C$_\alpha$H | 3.8 | 42.1 |
| Ornithine$^5$ | HN | 8.15 | — |
| Orn$^5$ | C$_\alpha$H | 4.46 | 51.2 |
|  | C$_\beta$H$_2$ | 1.58/1.42 | 27.5 |
|  | C$_\gamma$H$_2$ | 1.49/1.4 | 23.2 |
|  | C$_\delta$H$_2$ | 2.74 | 39 |
|  | NH$_2$ | — | — |
| Pro$^6$ | C$_\alpha$H | 4.10 | 60.4 |
|  | C$_\beta$H$_2$ | 1.98/1.60 | 29.5 |
|  | C$_\gamma$H$_2$ | 1.72 | 24.3 |
|  | C$_\delta$H$_2$ | 3.48/3.38 | 47.7 |

TABLE 1-continued

Chemical shifts of Odilomycin A (water, 280K)

| Spin system | Group | $^1$H (ppm) | $^{13}$C (ppm) |
|---|---|---|---|
| His$^7$ | HN | 8.49 | — |
| | C$_\alpha$H | 4.46 | 52.0 |
| | C$_\beta$H$_2$ | 2.98-2.91 | 26.3 |
| | C$_{\delta 2}$H | 7.03 | 118 |
| | C$_{\epsilon 1}$H$_2$ | 8.33 | 134 |
| δ Hydroxy lysine$^8$ Dhl$^8$ | HN | 8.41 | — |
| | C$_\alpha$H | 4.12 | 53.8 |
| | C$_\beta$H$_2$ | 1.70 | 27.0 |
| | C$_\gamma$H$_2$ | 1.36/1.26 | 30.0 |
| | C$_\delta$H-OH | 3.62 | 67.0 |
| | C$_\epsilon$H$_2$ | 2.86/2.63 | 44.5 |
| | NH$_2$ | — | — |
| dehydro arginine$^9$ Dha$^9$ | HN | 9.6 | — |
| | C$_\alpha$ | — | — |
| | C$_\beta$HC$_\gamma$H$_2$ | 6.17 | 132 |
| | C$_\delta$H$_2$ | 2.20 | 26.5 |
| | HN$_\epsilon$ | 3.10 | 39.5 |
| | C(NH$_2$) = NH | 7.0 | — |
| | | — | — |
| δ Hydroxy lysine$^{10}$ Dhl$^{10}$ | HN | 8.05 | |
| | C$_\alpha$H | 4.06 | 54.0 |
| | C$_\beta$H$_2$ | 1.65 | 27.0 |
| | C$_\gamma$H$_2$ | 1.27 | 30.0 |
| | C$_\delta$H-OH | 3.60 | 67.0 |
| | C$_\epsilon$H$_2$ | 2.86/2.63 | 44.5 |
| | NH$_2$ | — | — |
| Diaminobutane$^{11}$ Dbt$^{11}$ | HN | 8.05 | |
| | C$_\alpha$H$_2$ | 2.95 | 39.5 |
| | C$_\beta$H$_2$ | 1.30 | 25.3 |
| | C$_\gamma$H$_2$ | 1.40 | 24.0 |
| | C$_\delta$H$_2$ | 2.78 | 39.0 |
| | NH$_2$ | — | — |

TABLE 2

Chemical shifts of Odilomycin B (water, 280K)

| Spin system | Group | $^1$H (ppm) | $^{13}$C (ppm) |
|---|---|---|---|
| Lys$^1$ | HN | — | — |
| | C$_\alpha$H | 3.8 | 53.0 |
| | C$_\beta$H$_2$ | 1.66/1.62 | 30.4 |
| | C$_\gamma$H$_2$ | 1.2 | 21.1 |
| | C$_\delta$H$_2$ | 1.45 | 26.3 |
| | C$_\epsilon$H$_2$ | 2.78 | 39.0 |
| Hydroxy Diamino butyric acid$^2$ Dab(βOH)$^2$ | HN | 8.83 | — |
| | C$_\alpha$H | 4.28 | 56.3 |
| | C$_\beta$H-OH | 3.89 | 67.4 |
| | C$_\gamma$H$_2$ | 2.99/2.79 | 41.9 |
| | NH$_2$ | | |
| Hydroxy Diamino butyric acid$^3$ Dab(βOH)$^3$ | HN | 8.63 | — |
| | C$_\alpha$H | 4.33 | 56.3 |
| | C$_\beta$H-OH | 3.93 | 67.7 |
| | C$_\gamma$H$_2$ | 2.98/2.80 | 41.5 |
| | NH$_2$ | — | — |
| Gly$^4$ | HN | 8.37 | — |
| | C$_\alpha$H | 3.8 | 42.1 |
| Ornithine$^5$ Orn$^5$ | HN | 8.15 | — |
| | C$_\alpha$H | 4.46 | 51.2 |
| | C$_\beta$H$_2$ | 1.58/1.42 | 27.5 |
| | C$_\gamma$H$_2$ | 1.49/1.4 | 23.2 |
| | C$_\delta$H$_2$ | 2.74 | 39 |
| | NH$_2$ | — | — |
| Pro$^6$ | C$_\alpha$H | 4.10 | 60.4 |
| | C$_\beta$H$_2$ | 1.98/1.60 | 29.5 |
| | C$_\gamma$H$_2$ | 1.72 | 24.3 |
| | C$_\delta$H$_2$ | 3.48/3.38 | 47.7 |
| His$^7$ | HN | 8.49 | — |
| | C$_\alpha$H | 4.46 | 52.0 |
| | C$_\beta$H$_2$ | 2.98-2.91 | 26.3 |
| | C$_{\delta 2}$H | 7.03 | 118 |
| | C$_{\epsilon 1}$H | 8.33 | 134 |

TABLE 2-continued

Chemical shifts of Odilomycin B (water, 280K)

| Spin system | Group | $^1$H (ppm) | $^{13}$C (ppm) |
|---|---|---|---|
| Lys$^8$ | HN | 8.41 | — |
| | C$_\alpha$H | 4.12 | 53.8 |
| | C$_\beta$H$_2$ | 1.70 | 27.0 |
| | C$_\gamma$H$_2$ | 1.36/1.26 | 30.0 |
| | C$_\delta$H$_2$ | 1.53 | 26.4 |
| | C$_\epsilon$H$_2$ | 2.86/2.63 | 44.5 |
| | NH$_2$ | — | — |
| dehydro arginine$^9$ Dha$^9$ | HN | 9.6 | — |
| | C$_\alpha$ | — | — |
| | C$_\beta$HC$_\gamma$H$_2$ | 6.17 | 132 |
| | C$_\delta$H$_2$ | 2.20 | 26.5 |
| | HN$_\epsilon$ | 3.10 | 39.5 |
| | C(NH$_2$) = NH | 7.0 | — |
| | | — | — |
| δ Hydroxy lysine$^{10}$ Dhl$^{10}$ | HN | 8.05 | |
| | C$_\alpha$H | 4.06 | 54.0 |
| | C$_\beta$H$_2$ | 1.65 | 27.0 |
| | C$_\gamma$H$_2$ | 1.27 | 30.0 |
| | C$_\delta$H-OH | 3.60 | 67.0 |
| | C$_\epsilon$H$_2$ | 2.86/2.63 | 44.5 |
| | NH$_2$ | — | — |
| Diaminobutane$^{11}$ Dbt$^{11}$ | HN | 8.05 | |
| | C$_\alpha$H$_2$ | 2.95 | 39.5 |
| | C$_\beta$H$_2$ | 1.30 | 25.3 |
| | C$_\gamma$H$_2$ | 1.40 | 24.0 |
| | C$_\delta$H$_2$ | 2.78 | 39.0 |
| | NH$_2$ | — | — |

TABLE 3

Chemical shifts of Odilomycin C (water, 280K)

| Spin system | Group | $^1$H (ppm) | $^{13}$C (ppm) |
|---|---|---|---|
| Lys$^1$ | HN | — | — |
| | C$_\alpha$H | 3.8 | 53.0 |
| | C$_\beta$H$_2$ | 1.66/1.62 | 30.4 |
| | C$_\gamma$H$_2$ | 1.2 | 21.1 |
| | C$_\delta$H$_2$ | 1.45 | 26.3 |
| | C$_\epsilon$H$_2$ | 2.78 | 39.0 |
| Hydroxy Diamino butyric acid$^2$ Dab(βOH)$^2$ | HN | 8.83 | — |
| | C$_\alpha$H | 4.28 | 56.3 |
| | C$_\beta$H-OH | 3.89 | 67.4 |
| | C$_\gamma$H$_2$ | 2.99/2.79 | 41.9 |
| | NH$_2$ | | |
| Hydroxy Diamino butyric acid$^3$ Dab(βOH)$^3$ | HN | 8.63 | — |
| | C$_\alpha$H | 4.33 | 56.3 |
| | C$_\beta$H-OH | 3.93 | 67.7 |
| | C$_\gamma$H$_2$ | 2.98/2.80 | 41.5 |
| | NH$_2$ | — | — |
| Gly$^4$ | HN | 8.37 | — |
| | C$_\alpha$H | 3.8 | 42.1 |
| Ornithine$^5$ Orn$^5$ | HN | 8.15 | — |
| | C$_\alpha$H | 4.46 | 51.2 |
| | C$_\beta$H$_2$ | 1.58/1.42 | 27.5 |
| | C$_\gamma$H$_2$ | 1.49/1.4 | 23.2 |
| | C$_\delta$H$_2$ | 2.74 | 39 |
| | NH$_2$ | — | — |
| Pro$^6$ | C$_\alpha$H | 4.10 | 60.4 |
| | C$_\beta$H$_2$ | 1.98/1.60 | 29.5 |
| | C$_\gamma$H$_2$ | 1.72 | 24.3 |
| | C$_\delta$H$_2$ | 3.48/3.38 | 47.7 |
| His$^7$ | HN | 8.49 | — |
| | C$_\alpha$H | 4.46 | 52.0 |
| | C$_\beta$H$_2$ | 2.98-2.91 | 26.3 |
| | C$_{\delta 2}$H | 7.03 | 118 |
| | C$_{\epsilon 1}$H | 8.33 | 134 |

TABLE 3-continued

Chemical shifts of Odilomycin C (water, 280K)

| Spin system | Group | $^1$H (ppm) | $^{13}$C (ppm) |
|---|---|---|---|
| Lys$^8$ | HN | 8.41 | — |
| | C$_\alpha$H | 4.12 | 53.8 |
| | C$_\beta$H$_2$ | 1.70 | 27.0 |
| | C$_\gamma$H$_2$ | 1.36/1.26 | 30.0 |
| | C$_\delta$H$_2$ | 1.53 | 26.4 |
| | C$_\epsilon$H$_2$ | 2.86/2.63 | 44.5 |
| | NH$_2$ | — | — |
| dehydro arginine$^9$ | HN | 9.6 | — |
| Dha$^9$ | C$_\alpha$ | — | — |
| | C$_\beta$HC$_\gamma$H$_2$ | 6.17 | 132 |
| | C$_\delta$H$_2$ | 2.20 | 26.5 |
| | HN$_\epsilon$ | 3.10 | 39.5 |
| | C(NH$_2$) = NH | 7.0 | — |
| Lys$^{10}$ | HN | 8.05 | — |
| | C$_\alpha$H | 4.06 | 54.0 |
| | C$_\beta$H$_2$ | 1.65 | 27.0 |
| | C$_\gamma$H$_2$ | 1.27 | 30.0 |
| | C$_\delta$H-OH | 1.58 | 26.3 |
| | C$_\epsilon$H$_2$ | 2.86/2.63 | 44.5 |
| | NH$_2$ | — | — |
| Diaminobutane$^{11}$ | HN | 8.05 | — |
| Dbt$^{11}$ | C$_\alpha$H$_2$ | 2.95 | 39.5 |
| | C$_\beta$H$_2$ | 1.30 | 25.3 |
| | C$_\gamma$H$_2$ | 1.40 | 24.0 |
| | C$_\delta$H$_2$ | 2.78 | 39.0 |
| | NH$_2$ | — | — |

TABLE 4

Key fragmentations of the 1297[M + H]$^+$ ions of Odilomycin A

| | |
|---|---|
| 172 | [Gly$^4$/Orn$^5$]$^+$ |
| 233 | [Dab($\beta$OH)$^2$/Dab($\beta$OH)$^3$]$^+$ |
| 235 | [Pro$^6$/His$^7$]$^+$ |
| 245 | [Lys$^1$/Dab($\beta$OH)$^2$]$^+$ |
| 282 | [His$^7$/Dhl$^8$]$^+$ |
| 299 | [Dhl$^8$/Dha$^9$]$^+$ or [Dha$^9$/Dhl$^{10}$]$^-$ |
| 361 | [Lys$^1$/Dab($\beta$OH)$^2$/Dab($\beta$OH)$^3$]$^+$ |
| 370 | [Dha$^9$/Dhl$^{10}$/Dbt$^{11}$] − NH3$^+$ |
| 379 | [Pro$^6$/His$^7$/Dhl$^8$]$^+$ |
| 396 | [Pro$^6$/His$^7$/Dhl$^8$]$^+$ + NH3$^+$ |
| 406 | [Gly$^4$/Orn$^5$/Pro$^6$/His$^7$]$^+$ |
| 436 | [His$^7$/Dhl$^8$/Dha$^9$]$^+$ |
| 530 | [Dhl$^8$/Dha$^9$/Dhl$^{10}$/Dbt$^{11}$]$^+$ |
| 533 | [Lys$^1$/Dab($\beta$OH)$^2$/Dab($\beta$OH)$^3$/Gly$^4$/Orn$^5$]$^+$ or [Pro$^6$/His$^7$/Dhl$^8$/Dha$^9$]$^+$ |
| 550 | [Gly$^4$/Orn$^5$/Pro$^6$/His$^7$/Dhl$^8$]$^+$ |
| 567 | [Gly$^4$/Orn$^5$/Pro$^6$/His$^7$/Dhl$^8$]$^+$ + NH3$^+$ |
| 683 | [Dab($\beta$OH)$^3$/Gly$^4$/Orn$^5$/Pro$^6$/His$^7$/Dhl$^8$]$^+$ + NH3$^+$ |
| 704 | [Gly$^4$/Orn$^5$/Pro$^6$/His$^7$/Dhl$^8$/Dha$^9$]$^+$ |
| 765 | [Pro$^6$/His$^7$/Dhl$^8$/Dha$^9$/Dhl$^{10}$/Dbt$^{11}$]$^+$ |
| 820 | [Dab($\beta$OH)$^3$/Gly$^4$/Orn$^5$/Pro$^6$/His$^7$/Dhl$^8$/Dha$^9$]$^+$ |
| 936 | [Gly$^4$/Orn$^5$/Pro$^6$/His$^7$/Dhl$^8$/Dha$^9$/Dhl$^{10}$/Dbt$^{11}$]$^+$ |
| 964 | [Dab($\beta$OH)$^3$/Gly$^4$/Orn$^5$/Pro$^6$/His$^7$/Dhl$^8$/Dha$^9$/Dhl$^{10}$]$^+$ |
| 1052 | [Dab($\beta$OH)$^3$/Gly$^4$/Orn$^5$/Pro$^6$/His$^7$/Dhl$^8$/Dha$^9$/Dhl$^{10}$/Dbt$^{11}$]$^+$ |
| 1064 | [Lys$^1$/Dab($\beta$OH)$^2$/Dab($\beta$OH)$^3$/Gly$^4$/Orn$^5$/Pro$^6$/His$^7$/Dhl$^8$/Dha$^9$]$^+$ |
| 1297 | [Lys$^1$/Dab($\beta$OH)$^2$/Dab($\beta$OH)$^3$/Gly$^4$/Orn$^5$/Pro$^6$/His$^7$/Dhl$^8$/Dha$^9$/Dhl$^{10}$/Dbt$^{11}$]$^+$ |

TABLE 5

Key fragmentations of the 1281[M + H]$^+$ ions of Odilomycin B

| | |
|---|---|
| 172 | [Gly$^4$/Orn$^5$]$^+$ |
| 233 | [Dab($\beta$OH)$^2$/Dab($\beta$OH)$^3$]$^+$ |
| 235 | [Pro$^6$/His$^7$]$^+$ |
| 245 | [Lys$^1$/Dab($\beta$OH)$^2$]$^+$ |
| 266 | [His$^7$/Lys$^8$]$^+$ |
| 361 | [Lys$^1$/Dab($\beta$OH)$^2$/Dab($\beta$OH)$^3$]$^+$ |
| 370 | [Dha$^9$/Dhl$^{10}$/Dbt$^{11}$]$^+$ − NH3$^+$ |
| 363 | [Pro$^6$/His$^7$/Lys$^8$]$^+$ |
| 380 | [Pro$^6$/His$^7$/Lys$^8$]$^+$ + NH3$^+$ |
| 406 | [Gly$^4$/Orn$^5$/Pro$^6$/His$^7$]$^+$ |
| 514 | [Lys$^8$/Dha$^9$/Dhl$^{10}$/Dbt$^{11}$]$^+$ |
| 517 | [Pro$^6$/His$^7$/Lys$^8$/Dha$^9$]$^+$ |
| 533 | [Lys$^1$/Dab($\beta$OH)$^2$/Dab($\beta$OH)$^3$/Gly$^4$/Orn$^5$]$^+$ |
| 534 | [Gly$^4$/Orn$^5$/Pro$^6$/His$^7$/Lys$^8$]$^+$ |
| 551 | [Gly$^4$/Orn$^5$/Pro$^6$/His$^7$/Lys$^8$]$^+$ + NH3$^+$ |
| 667 | [Dab($\beta$OH)$^3$/Gly$^4$/Orn$^5$/Pro$^6$/His$^7$/Lys$^8$]$^+$ + NH3$^+$ |
| 688 | [Gly$^4$/Orn$^5$/Pro$^6$/His$^7$/Lys$^8$/Dha$^9$]$^+$ |
| 749 | [Pro$^6$/His$^7$/Lys$^8$/Dha$^9$/Dhl$^{10}$/Dbt$^{11}$]$^+$ |
| 804 | [Dab($\beta$OH)$^3$/Gly$^4$/Orn$^5$/Pro$^6$/His$^7$/Lys$^8$/Dha$^9$]$^+$ |
| 920 | [Gly$^4$/Orn$^5$/Pro$^6$/His$^7$/Lys$^8$/Dha$^9$/Dhl$^{10}$/Dbt$^{11}$]$^+$ |
| 948 | [Dab($\beta$OH)$^3$/Gly$^4$/Orn$^5$/Pro$^6$/His$^7$/Lys$^8$/Dha$^9$/Dhl$^{10}$]$^+$ |
| 1036 | [Dab($\beta$OH)$^3$/Gly$^4$/Orn$^5$/Pro$^6$/His$^7$/Lys$^8$/Dha$^9$/Dhl$^{10}$/Dbt$^{11}$]$^+$ |
| 1048 | [Lys$^1$/Dab($\beta$OH)$^2$/Dab($\beta$OH)$^3$/Gly$^4$/Orn$^5$/Pro$^6$/His$^7$/lys$^8$/Dha$^9$]$^+$ |
| 1281 | [Lys$^1$/Dab($\beta$OH)$^2$/Dab($\beta$OH)$^3$/Gly$^4$/Orn$^5$/Pro$^6$/His$^7$/lys$^8$/Dha$^9$/Dhl$^{10}$/Dbt$^{11}$]$^+$ |

TABLE 6

Key fragmentations of the 1264[M + H]$^+$ ions of Odilomycin C

| | |
|---|---|
| 172 | [Gly$^4$/Orn$^5$]$^+$ |
| 233 | [Dab($\beta$OH)$^2$/Dab($\beta$OH)$^3$]$^+$ |
| 235 | [Pro$^6$/His$^7$]$^+$ |
| 245 | [Lys$^1$/Dab($\beta$OH)$^2$]$^+$ |
| 266 | [His$^7$/Lys$^8$]$^+$ |
| 361 | [Lys$^1$/Dab($\beta$OH)$^2$/Dab($\beta$OH)$^3$]$^+$ |
| 354 | [Dha$^9$/Lys$^{10}$/Dbt$^{11}$]$^+$ − NH3$^+$ |
| 363 | [Pro$^6$/His$^7$/Lys$^8$]$^+$ |
| 380 | [Pro$^6$/His$^7$/Lys$^8$]$^+$ + NH3$^+$ |
| 406 | [Gly$^4$/Orn$^5$/Pro$^6$/His$^7$]$^+$ |
| 498 | [Lys$^8$/Dha$^9$/Lys$^{10}$/Dbt$^{11}$]$^+$ |
| 517 | [Pro$^6$/His$^7$/Lys$^8$/Dha$^9$]$^+$ |
| 533 | [Lys$^1$/Dab($\beta$OH)$^2$/Dab($\beta$OH)$^3$/Gly$^4$/Orn$^5$]$^+$ |
| 534 | [Gly$^4$/Orn$^5$/Pro$^6$/His$^7$/Lys$^8$]$^+$ |
| 551 | [Gly$^4$/Orn$^5$/Pro$^6$/His$^7$/Lys$^8$]$^+$ + NH3$^+$ |
| 688 | [Gly$^4$/Orn$^5$/Pro$^6$/His$^7$/Lys$^8$/Dha$^9$]$^+$ |
| 733 | [Pro$^6$/His$^7$/Lys$^8$/Dha$^9$/Lys$^{10}$/Dbt$^{11}$]$^+$ |
| 804 | [Dab($\beta$OH)$^3$/Gly$^4$/Orn$^5$/Pro$^6$/His$^7$/Lys$^8$/Dha$^9$]$^+$ |
| 904 | [Gly$^4$/Orn$^5$/Pro$^6$/His$^7$/Lys$^8$/Dha$^9$/Lys$^{10}$/Dbt$^{11}$]$^+$ |
| 932 | [Dab($\beta$OH)$^3$/Gly$^4$/Orn$^5$/Pro$^6$/His$^7$/Lys$^8$/Dha$^9$/Lys$^{10}$]$^+$ |
| 1020 | [Dab($\beta$OH)$^3$/Gly$^4$/Orn$^5$/Pro$^6$/His$^7$/Lys$^8$/Dha$^9$/Lys$^{10}$/Dbt$^{11}$]$^+$ |
| 1048 | [Lys$^1$/Dab($\beta$OH)$^2$/Dab($\beta$OH)$^3$/Gly$^4$/Orn$^5$/Pro$^6$/His$^7$/Lys$^8$/Dha$^9$]$^+$ |
| 1265 | [Lys$^1$/Dab($\beta$OH)$^2$/Dab($\beta$OH)$^3$/Gly$^4$/Orn$^5$/Pro$^6$/His$^7$/lys$^8$/Dha$^9$/Lys$^{10}$/Dbt$^{11}$]$^+$ |

Example 4

In Vitro Studies

Antibacterial Susceptibility Testing Methods

The minimal inhibitory concentrations (MIC) were determined according to the Clinical and Laboratory Standards Institute (CLSI) conditions guidelines detailed in Table 7. Assays were performed in triplicate.

TABLE 7

MIC determination parameters

| Strain(s) | Relevant CLSI guidelines | Growth Media and Incubation Conditions |
|---|---|---|
| *Acinetobacter baumannii*<br>*Bacillus subtilis*<br>*Enterobacter cloacae*<br>*Enterococcus faecalis*<br>*Enterococcus faecium*<br>*Escherichia coli*<br>*Klebsiella pneumonia*<br>*Klebsiella oxytoca*<br>*Pseudomonas aeruginosa*<br>*Staphylococcus aureus*<br>*Staphylococcus epidermidis*<br>*Stenotrophomonas maltophilia* | M07-A8. Methods for Dilution Antimicrobial Susceptibility Tests for Bacteria That Grow Aerobically; Approved Standard-Eighth Edition | Mueller-Hinton Broth (MH)<br>37° C.<br>aerobic<br>18-24 h |
| *Streptococcus pneumonia*<br>*Streptococcus pyogenes* | M07-A8 | MH plus 5% Lysed Horse Blood (MHB)<br>37° C.<br>aerobic<br>18-24 h |
| *Haemophilus influenzae* | M07-A8 | Haemophilus Test Medium (HTM)<br>37° C.<br>Aerobic<br>18-24 h. |
| *Moraxella catarrhalis* | M45-A2. Methods for Antimicrobial Dilution and Disk Susceptibility Testing of Infrequently Isolated or Fastidious Bacteria; Approved Guideline-Second Edition | MH<br>37° C.<br>aerobic<br>24 h. |
| *Pasteurella multocida* | M45-A2 | MHB<br>37° C.<br>aerobic<br>24 h. |
| *Mannheimia haemolytica* | None available, followed M07-A8 | MHB<br>37° C.<br>aerobic<br>24 h. |
| *Proprionibacterium acnes*<br>*Bacteroides fragilis* | M11-A7. Methods for Antimicrobial Susceptibility Testing of Anaerobic Bacteria; Approved Standard-Seventh Edition | Schaedler Broth plus 1 µg/ml vitamin K1 and 5% lysed horse blood (SB)<br>37° C.<br>anaerobic<br>48 h. |

Preparation of Inocula. Five to 10 well-isolated colonies were picked and resuspended in 3 ml sterile saline. The inoculum was re-suspended by vigorous shaking on a vortex mixer for 15 s. Turbidity was adjusted to McFarland standard 0.5 ($1-5 \times 10^6$ CFU/ml). The inoculum was further diluted in the appropriate media (Table 7) to give a final inoculum in each well of ~$2-8 \times 10^5$ CFU/ml.

Addition of Test Article. Stock solutions of Odilomycin A or comparator were diluted in the appropriate media to give a maximum starting concentration of 50 µg/mL in the assay. 50 µL of medium was dispensed into each well in columns two to 12 of a 96 well plate. 100 µL of the appropriate test compound solution (100 µg/mL) was dispensed into each well in column one. In the case of *M. catarrhalis, M. haemolytica* and *P. multocida* these values were doubled (a final assay volume of 200 µL was used). Serial two-fold dilutions were performed from column one to column 10 to give a concentration range of 50 to 0.1 µg/mL of each compound in the assay. Columns 11 and 12 served as positive (no drug or test article, inoculum added), and negative (no drug, test article, or inoculum added) growth controls respectively.

Addition of Bacterial Strains. 50 µL of each inoculum suspension was added to the appropriate wells, resulting in a final volume of 100 µL consisting of 50 µL diluted compound or diluents, and 50 µL of inoculum or broth alone.

Minimal bactericidal concentrations (MBCs) were established by extending the MIC procedure to the evaluation of bactericidal activity. After 24 hours, 10 µL were drawn from the wells, serially diluted and then spotted onto suitable agar plates. The plates were incubated at 37° C. overnight. The MBC was read 18 h later as the lowest concentration of antibiotic which resulted in 0.1% survival in the subculture. All the experiments were done in triplicate.

MBCs were also determined in presence of 50% and 95% (v/v) of human serum to assess protein binding.

Bactericidal Effects of Odilomycin on Growing *S. aureus* and *P. aeruginosa*

Bacterial killing curves were carried out by inoculating *S. aureus* ATCC 13709 and *P. aeruginosa* ATCC 27853 with Odilomycin A concentration equal to four-fold the MIC. Vancomycin or Polymixin were used at four-fold their MIC. *S. aureus* and *P. aeruginosa* inoculi were prepared from colonies grown overnight in MHB. Antibiotics concentrations in the flask were adjusted in MHB according to the desired concentration. Culture tubes containing 10 mL were inoculated with *S. aureus* or *P. aeruginosa* at an approximate inoculum of $10^5$ CFU/mL. Samples were drawn and bacteria were counted at 0, 1, 2, 3, 4, 6 and 24 h of incubation at 37° C. Thus, after vortexing the culture tubes, two 50 µL samples were removed and serially diluted with MHB. After each dilution step, 20 μL was plated onto LB agar plates, which were incubated for 24 h at 37° C. Afterwards the colonies were counted and back-extrapolated to the original volume to determine the initial concentration (CFU/mL).

In Vitro Biological Properties

Odilomycin A was tested for antimicrobial activity against a wide range of bacteria involved in nosocomial and animal infection. It owns a wide spectrum of antibacterial activity against Gram-positive and Gram-negative pathogens (Table 8). With respect to Gram-positive bacteria, the antibacterial activities of Odilomycin A are strong, with MICs inferior to 1 μg/mL against *S. aureus, S. epidermidis*, and *B. subtilis* strains, including against some multiresistant clinical isolates (Table 9). Weak or no antibacterial activity was observed against *E. faecalis, E. faecium, S. pneumoniae*, and *S. pyogenes*. With respect to Gram-negative bacteria, the antibacterial activities of Odilomycin A is strong against *K. pneumoniae* and *K. oxytoca*, and is good, with MICs inferior to 10 μg/mL against *A. baumannii, E. cloacae, E. coli, M. catarrhalis, P. aeruginosa*, and *S. maltophilia* strains, including some multiresistant clinical isolates (Table 8, Table 9).

TABLE 8

Antibacterial activity of Odilomycins A, B, C

| Bacteria | Strain | Odilomycin A | Odilomycin B | Odilomycin C | Control |
|---|---|---|---|---|---|
| Gram (−) | | | | | |
| *A. baumannii* | ATCC BAA747 | 6.25 | — | — | <0.1[a] |
| *B. fragilis* | ATCC 25238 | 1.56 | — | — | 0.39[b] |
| *E. cloacae** | 11370 | 1.56 | — | — | 0.78[c] |
| *E. coli* | ATCC 25922 | 3.13 | — | — | 0.39[c] |
| *E. coli* CTX-M14* | AEC7 | 3.13 | — | — | 0.39[c] |
| *E. coli* CTX-M15* | MEC23 | 3.13 | — | — | 0.39[c] |
| *E. coli* TEM* | MEC12 | 1.56 | — | — | 0.39[c] |
| *K. pneumoniae* | ATCC 43816 | 0.78 | — | — | 0.39[c] |
| *K. pneumoniae* KPC* | 2475 | 1.56 | — | — | 0.78[c] |
| *K. oxytoca** | NEB9 | 0.39 | — | — | 0.39[c] |
| *M. haemolytica* | ATCC 33396 | 50.0 | — | — | <0.1[a] |
| *M. catarrhalis* | ATCC 25238 | 1.56 | — | — | <0.1[a] |
| *P. multocida* | ATCC 12945 | 25.0 | — | — | <0.1[a] |
| *P. aeruginosa* | ATCC 27853 | 3.13 | 3.13 | 6.25 | 0.39[c] |
| *S. maltophilia* | ATCC | 6.25 | — | — | <0.1[a] |
| *H. influenzae* | ATCC 49766 | 12.5 | — | — | <0.1[a] |
| Gram (+) | | | | | |
| *B. subtilis* | DSM 347 | <0.20 | — | — | 0.20[d] |
| *E. faecalis* | ATCC 29212 | >50.0 | — | — | 0.78[a] |
| *E. faecium* | ATCC 700221 | 25.0 | — | — | >50.0[a] |
| *S. pneumoniae* | ATCC 49619 | >50.0 | — | — | 0.39[a] |
| *S. pyogenes* | ATCC 12384 | 50.0 | — | — | 0.20[a] |
| *S. aureus* | ATCC 13709 | 0.39 | 0.39 | 0.78 | 0.78[d] |
| *S. aureus* | ATCC 25923 | 0.39 | 0.39 | 0.78 | 0.78[d] |
| *S. aureus* USA300 | ATCC BAA-1556 | 0.78 | 0.78 | 1.56 | 0.78[d] |
| *S. epidermidis* | ATCC 12228 | <0.20 | — | — | 0.20[d] |
| *P. acnes* | ATCC 6919 | 3.13 | — | — | 0.39[a] |

*clinical isolate from University Hospital of Nimes;
[a]ciprofloxacin;
[b]metronidazole;
[c]polymyxin;
[d]vancomycin

TABLE 9

Antibacterial activity of Odilomycin A against multiresistant clinical isolates

| | P. aeruginosa | | | | | S. aureus | | | | |
|---|---|---|---|---|---|---|---|---|---|---|
| Antibacterial | 5618 | 401681 | 35170 | 42162 | 512232 | 23305 | 16666 | 20681 | 21840 | 20364 |
| Pip./Taz.[a] | S | S | S | S | R | — | — | — | — | — |
| Ticar./CA[b] | S | R | R | R | R | — | — | — | — | — |
| Erythromycin | R | R | R | R | R | R | R | S | S | R |
| Cefepim | S | S | S | S | S | — | — | — | — | — |
| Cefoxitin | — | — | — | — | — | I | R | R | S | R |
| Clindamycin | R | R | R | R | R | R | R | S | S | R |
| Imipenem | R | S | R | R | R | — | — | — | — | — |
| Gentamicin | R | R | R | R | R | R | R | S | S | S |
| Ciprofloxacin | R | S | R | R | R | R | S | R | S | R |
| Aztreonam | S | I | R | I | R | — | — | — | — | — |
| Vancomycin | — | — | — | — | — | S | S | S | S | S |
| Linezolid | — | — | — | — | — | S | S | S | S | S |
| Odilomycin A[d] | 6.25 | 25 | >50 | 25 | 3.12 | 0.78 | <0.19 | 1.56 | 0.39 | 0.78 |

[a]Piperacillin/Tazobactam,
[b]Ticarcillin/Clavulanic acid,
R: resistant,
S: sensitive,
I: intermediate.

MBCs of Odilomycins A-C were assessed on *S. aureus* and *P. aeruginosa*. These molecules revealed to be bactericidal (Table 9).

TABLE 10

Bactericidal activity of Odilomycins A, B, C

| | S. aureus ATCC 13709 | | P. aeruginosa ATCC 27853 | |
|---|---|---|---|---|
| Molecule | MIC (µg/mL) | MBC (µg/mL) | MIC (µg/mL) | MBC (µg/mL) |
| Odilomycin A | 0.39 | 0.78 | 3.12 | 6.25 |
| Odilomycin B | 0.39 | 0.78 | 3.12 | 3.12 |
| Odilomycin C | 0.78 | 1.56 | 6.25 | 12.5 |

Figure 3:
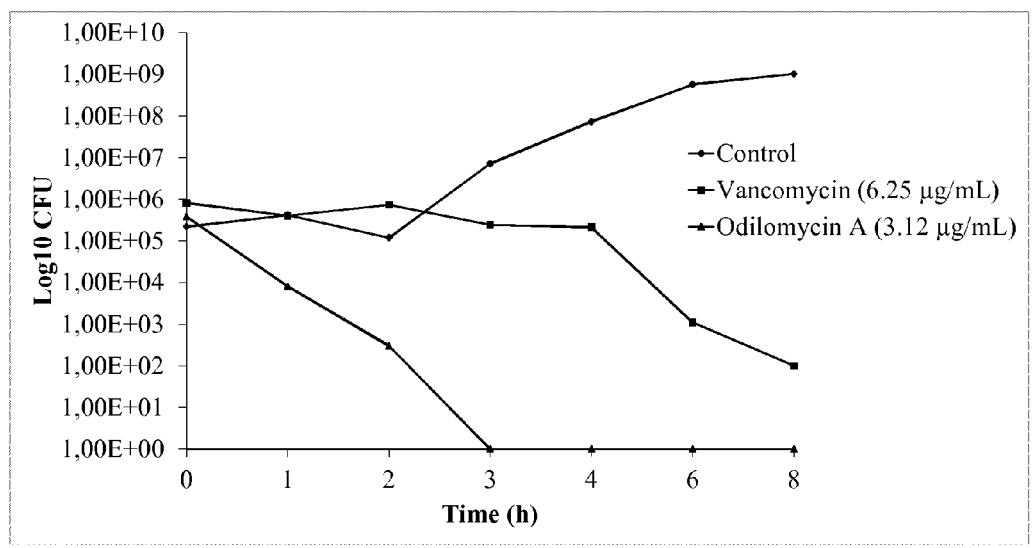
FIG. 3 shows bactericidal effects of Odilomycin A on growing *S. aureus* ATCC13709.
Figure 4:
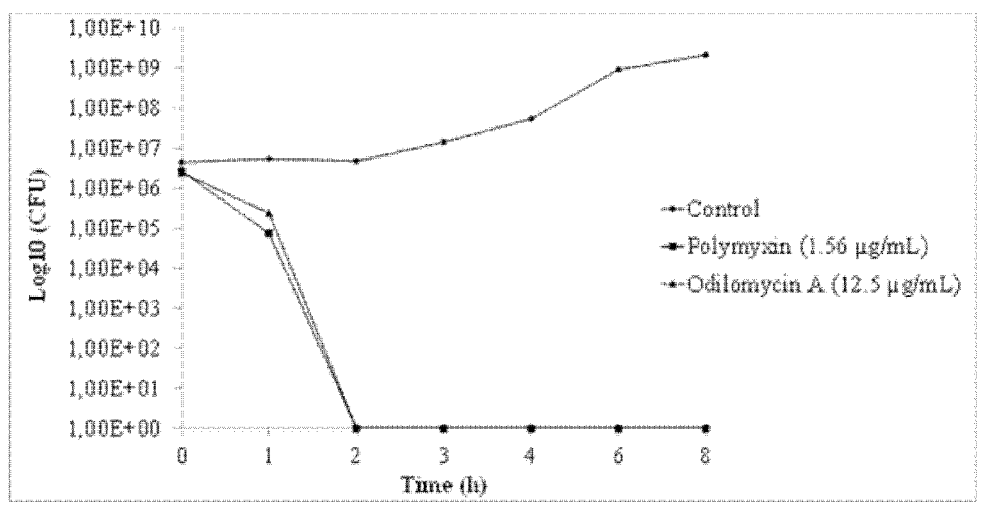
FIG. 4 shows bactericidal effects of Odilomycin A on growing *P. aeruginosa* ATCC27853.

Time-to-kill experiments were realized to assess the bactericidal effects of Odilomycin A on growing *S. aureus* and *P. aeruginosa*. At four-fold the MIC, Odilomycin A kills 100% of *P. aeruginosa* and *S. aureus* bacteria within 2 h and 3 h respectively, making this molecule a fast and powerful bactericidal agent (FIGS. 3 and 4).

MBC of Odilomycin A was assessed in presence of 50% (v/v) and 95% (v/v) human serum (Table 10). The results show that the antibacterial activity of the molecule is weakly affected by the presence of serum proteins.

TABLE 11

Effects of serum on the bactericidal activity of OdilomycinA

| Serum % (v/v) | MBC S. aureus ATCC 13709 |
|---|---|
| 0 | 0.78 |
| 50 | 1.56 |
| 95 | 1.56 |

Cytotoxicity Test

The cytotoxicity of the Odilomycins A-C was investigated against Human colon adenocarcinoma (HT29) cells and Human normal lung fibroblasts (MRC-5) cells. 200 µL of the cell suspension of HT29 (human colorectal adenocarcinoma) prepared in RPMI 1640+1% L-Glutamine supplemented with 10% (v/v) fetal calf serum and 200 µL of the cell suspension of MRC5 (human lung fibroblast) prepared in Dulbecco's modified Eagle's medium supplemented with 25 mM glucose and 10% (v/v) fetal calf serum were inoculated into 96-well plates.

The inoculating cell number was 800 cells per well for HT29 and 2100 cells per well for MRC-5. The microplates were incubated at 37° C. for 24 h with 5% of $CO_2$.

Twenty four hours later, Odilomycin A, B or C dissolved in water were added for 72 h at a final concentration from 0.78 µg/mL to 100 µg/mL in a fixed volume of water (1% final concentration). The number of viable cells measured at 490 nm with the MTS reagent (Promega, Madison, Wis.) and $LD_{50}$ was calculated as the concentration of compound eliciting a 50% inhibition of cell proliferation. Experiments were done in triplicate.

The $LD_{50}$ was superior to 100 µg/mL against both cell lines for each of Odilomycin A, B and C. 100% of cell viability was observed at a dose of up to 100 µg/mL.

Example 5

Studies on Synergy with Other Antimicrobials

In vitro interactions of Odilomycin A with rifampicin, ciprofloxacin, kanamycin, gentamicin, ampicillin, tetracycline and vancomycin were investigated by microdilution checkerboard technique using 96-well microtiter plates for each combination.

Vancomycin, rifampicin, kanamycin, gentamicin, ampicillin, ciprofloxacin and tetracycline (Sigma-Aldrich) were provided as standard powders by the manufacturers.

Serial two-fold dilutions of the antimicrobial agents in MHB were placed alone or in combination in wells and inoculated with an appropriate *S. aureus* ATCC 25923 inoculum or *K. pneumoniae* ATCC 43816 so that each well contained approximately $10^4$ CFU/mL. After incubation at 37° C. for 16-20 h, the MIC was considered as the well containing the lowest concentrations of the two drugs in which no visible growth was observed. Concentrations of each antimicrobial which were tested in combination were between ⅛×MIC and 2×MIC.

Synergy with Other Antimicrobials

The interactions of Odilomycin A with other antibiotics from different classes were investigated against *S. aureus* (Table 11). A synergistic interaction was observed with the aminoglycoside antibiotics kanamycin and gentamicin. This synergistic interaction was also observed against *K. pneumoniae* (Table 12).

TABLE 12

Synergistic interaction of Odilomycin A with antibiotics against *S. aureus*

| Antibiotic | MIC (μg/mL) antibiotic alone | Synergy with Odilomycin A | Combinations (μg/mL) Odilomycin/antibiotic |
|---|---|---|---|
| Odilomycin A | 0.39 | N/A | |
| Rifampicin | 0.012 | − | |
| Kanamycin | 0.62 | + | 0.19/0.31 |
| | | | 0.19/0.15 |
| | | | 0.09/0.31 |
| | | | 0.09/0.15 |
| Gentamicin | 0.078 | + | 0.19/0.039 |
| Ampicillin | 0.15 | − | |
| Tetracycline | 0.78 | − | |
| Vancomycin | 0.78 | − | |
| Ciprofloxacin | 0.31 | − | |

TABLE 13

Synergistic interaction of Odilomycin A with aminoglycosides against *K. pneumoniae*

| Antibiotic | MIC (μg/mL) antibiotic alone | Synergy with Odilomycin A | Combinations (μg/mL) Odilomycin/antibiotic |
|---|---|---|---|
| Odilomycin A | 25 | N/A | |
| Kanamycin | 1.56 | + | 6.25/0.39 |
| Gentamicin | 0.39 | + | 12.5/0.09 |
| | | | 3.12/.19 |

Example 6

In Vivo Studies

In Vivo Biological Activity of Odilomycin A

Female ICR mice ordered from Harlan Laboratories (Indianapolis, Ind.) weighing 19-21 g were used in experiments of acute lethal infection. Mice were fully immunocompetent. Infection was induced by inoculating intraperitoneally in mice a bacterial suspension of *S. aureus* Smith ATCC 13709. The bacterial challenges (ca 5 $\log_{10}$ CFU/mouse) were given suspended in 0.5 mL of 20% hog mucin. Treatments were administered once 1 hour after challenge via IV injection (Linezolid was administered immediately after challenge) (Table 13). Mortality was tracked out to 5 days post challenge. Animals that remained surviving at the end of the study were humanely euthanized.

TABLE 14

Challenge and dose schedule

| Group | n | *S. aureus* Challenge (CFU/mouse) | Treatment | Concentration (mg/kg) | Route | Dosing schedule |
|---|---|---|---|---|---|---|
| 1 | 6 | 5 $\log_{10}$ | None | N/A | N/A | N/A |
| 2 | 6 | 5 $\log_{10}$ | Linezolid | 12.5 | PO | 0 hr |
| 3 | 6 | 5 $\log_{10}$ | Odilomycin A | 5.0 | IV | 1 hr |
| 4 | 6 | 5 $\log_{10}$ | Odilomycin A | 2.5 | IV | 1 hr |
| 5 | 6 | 5 $\log_{10}$ | Odilomycin A | 1.0 | IV | 1 hr |

Female BALB/c mice ordered from Harlan Laboratories (Indianapolis, Ind.) weighing 19-21 g were used in experiments of acute lethal infection. Mice were fully immunocompetent. Infection was induced by inoculating intraperitoneally in mice a bacterial suspension of *P. aeruginosa* ATCC 27853. The bacterial challenges (8.6 $\log_{10}$ CFU/mouse) were given suspended in 0.1 mL sterile saline. Treatments were administered once 1 hour after challenge via IV injection (Tobramycin was administered via IP injection immediately after challenge) (Table 13). Mortality was tracked out to 2 days post challenge. Animals that remained surviving at the end of the study were humanely euthanized.

TABLE 15

Challenge and dose schedule

| Group | n | *P. aeruginosa* Challenge (CFU/mouse) | Treatment | Concentration (mg/kg) | Route | Dosing schedule |
|---|---|---|---|---|---|---|
| 1 | 6 | 8.6 $\log_{10}$ | None | N/A | N/A | N/A |
| 2 | 6 | 8.6 $\log_{10}$ | Tobramycin | 0.39 | IP | 0 hr |
| 3 | 6 | 8.6 $\log_{10}$ | Odilomycin A | 15 | IV | 1 hr |
| 4 | 6 | 8.6 $\log_{10}$ | Odilomycin A | 7.5 | IV | 1 hr |

In Vivo Biological Properties

Untreated animals died within 24-48 h after *S. aureus* infection. All mice treated with linezolid and Odilomycin A at doses of 5.0 mg/kg and 2.5 mg/kg survived up to 5 days after infection (Table 14). One mouse died with Odilomycin A at a dose of 1.0 mg/kg 2 days after infection.

TABLE 16

Survival of mice after *S. aureus* challenge and treatment

| Group | n | Treatment | Dose (mg/kg) | Day 0 | Day 1 | Day 2 | Day 3 | Day 4 | Day 5 |
|---|---|---|---|---|---|---|---|---|---|
| 1 | 6 | None | N/A | 0 | 6 | 0 | 0 | 0 | 0 |
| 2 | 6 | Linezolid | 12.5 | 0 | 0 | 0 | 0 | 0 | 0 |
| 3 | 6 | Odilomycin A | 5.0 | 0 | 0 | 0 | 0 | 0 | 0 |

TABLE 16-continued

Survival of mice after *S. aureus* challenge and treatment

| Group | n | Treatment | Dose (mg/kg) | Animal deaths |||||||
|---|---|---|---|---|---|---|---|---|---|
| | | | | Day 0 | Day 1 | Day 2 | Day 3 | Day 4 | Day 5 |
| 4 | 6 | Odilomycin A | 2.5 | 0 | 0 | 0 | 0 | 0 | 0 |
| 5 | 6 | Odilomycin A | 1.0 | 0 | 0 | 1 | 0 | 0 | 0 |

Untreated animals died within 24-48 h after *P. aeruginosa* infection. All mice treated with Tobramycin survived up to 5 days after infection (Table 14). One mouse died at day 1 with Odilomycin A at a dose of 15 mg/kg, and 4 mice died at day 1 with Odilomycin A at a dose of 7.5 mg/kg.

TABLE 17

Survival of mice after *P. aeruginosa* challenge and treatment

| Group | n | Treatment | Dose (mg/kg) | Animal deaths |||
|---|---|---|---|---|---|---|
| | | | | Day 0 | Day 1 | Day 2 |
| 1 | 6 | None | N/A | 0 | 6 | 0 |
| 2 | 6 | Tobramycin | 0.39 | 0 | 0 | 0 |
| 3 | 6 | Odilomycin A | 15 | 0 | 1 | 4 |
| 4 | 6 | Odilomycin A | 7.5 | 0 | 4 | 1 |

The invention claimed is:

1. A pharmaceutical composition comprising a compound of formula (I):

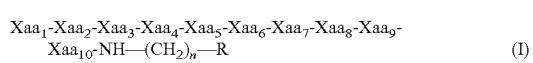

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}NH\text{—}(CH_2)_n\text{—}R \quad (I)$$

wherein $Xaa_1$, $Xaa_2$, $Xaa_3$, $Xaa_5$, $Xaa_7$, $Xaa_8$ and $Xaa_{10}$ are independently selected from the group consisting of lysine, 3-hydroxylysine, 4-hydroxylysine, 5-hydroxylysine, 3,4-dihydroxylysine, 3,5-dihydroxylysine, 4,5-dihydroxylysine, ornithine, 3-hydroxyornithine, 4-hydroxyornithine, 3,4-dihydroxyornithine, 2,4-diaminobutanoic acid, 3-hydroxy-2,4-diaminobutanoic acid, arginine, histidine, serine, and threonine;

$Xaa_4$ is glycine, 3-aminopropanoic acid, or 4-aminobutanoic acid;

$Xaa_6$ is proline, 3-hydroxyproline, 4-hydroxyproline, aziridine-2-carboxylic acid, azetidine-2-carboxylic acid, pipecolic acid, 4-oxaproline, 3-thiaproline, 4-thiaproline, 3,4-dehydroproline, 4-aminoproline, 4-fluoroproline, α-methylproline, or α-allylproline;

$Xaa_9$ is arginine, 2,3-dehydroarginine, citrulline, 2,3-dehydrocitrulline, canavanine, or 2,3-dehydrocanavanine;

n is 2, 3, 4, 5, 6, 7, 8, 9, or 10;

R is —OH, —NH$_2$, or —COOH, and an aminoglycoside antibiotic.

2. The Pharmaceutical composition of claim 1, wherein $Xaa_1$ is lysine;

$Xaa_2$ and $Xaa_3$ are each 3-hydroxy-2,4-diaminobutanoic acid;

$Xaa_4$ is glycine;

$Xaa_5$ is ornithine;

$Xaa_6$ is proline;

$Xaa_7$ is histidine; and $Xaa_9$ is 2,3-dehydroarginine.

3. The pharmaceutical composition of claim 1, wherein $Xaa_1$ is lysine;

$Xaa_2$ and $Xaa_3$ are each 3-hydroxy-2,4-diaminobutanoic acid;

$Xaa_4$ is glycine;

$Xaa_5$ is ornithine;

$Xaa_6$ is proline;

$Xaa_7$ is histidine;

$Xaa_8$ is lysine or 5-hydroxylysine;

$Xaa_9$ is 2,3-dehydroarginine; and $Xaa_{10}$ is lysine or 5-hydroxylysine.

4. The pharmaceutical composition of claim 1, wherein
Xaa$_1$ is lysine;
Xaa$_2$ and Xaa$_3$ are each 3-hydroxy-2,4-diaminobutanoic acid;
Xaa$_4$ is glycine;
Xaa$_5$ is ornithine;
Xaa$_6$ is proline;
Xaa$_7$ is histidine;
Xaa$_8$ is lysine or 5-hydroxylysine;
Xaa$_9$ is 2,3-dehydroarginine;
Xaa$_{10}$ is lysine or 5-hydroxylysine;
n is 4; and
R is NH$_2$.

5. The pharmaceutical composition of claim 1, wherein the compound is a compound of formula (Ia):

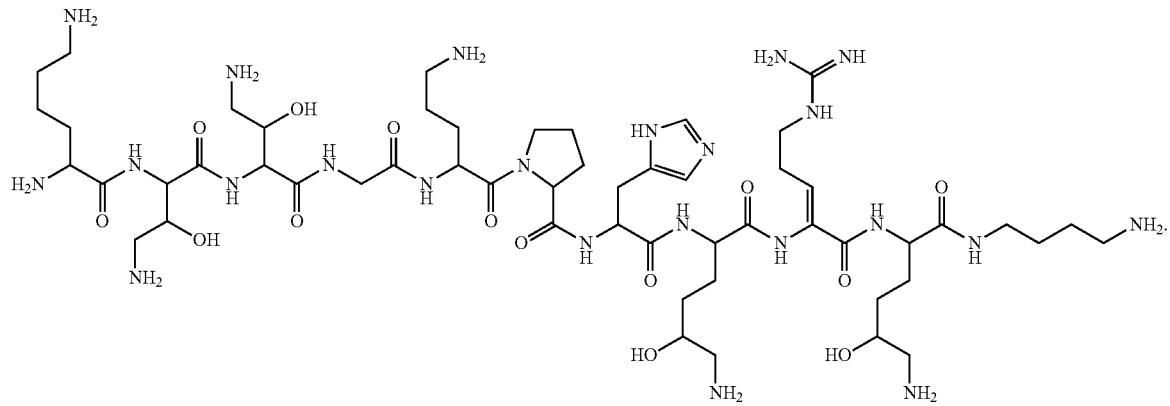

(Ia)

6. The pharmaceutical composition of claim 1, wherein the compound is a compound of formula (Ib):

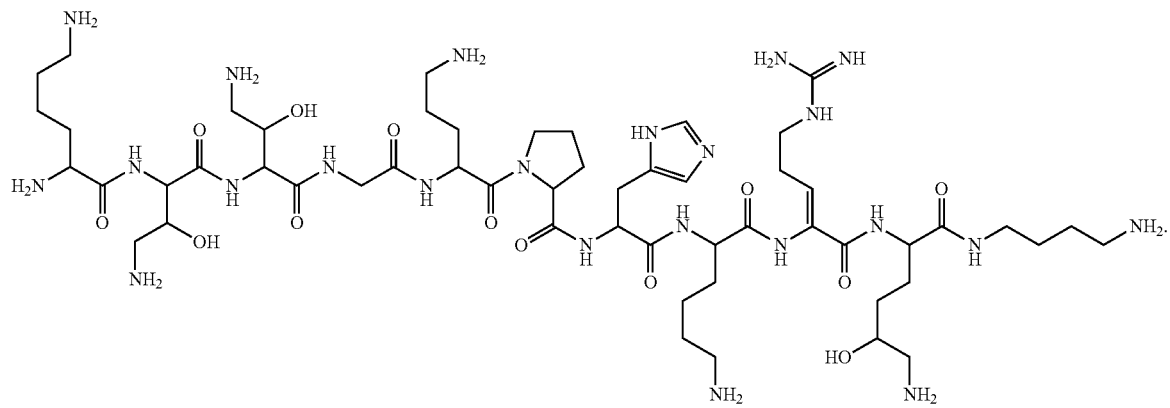

(Ib)

7. The pharmaceutical composition of claim 1, wherein the compound is a compound of formula (Ic):

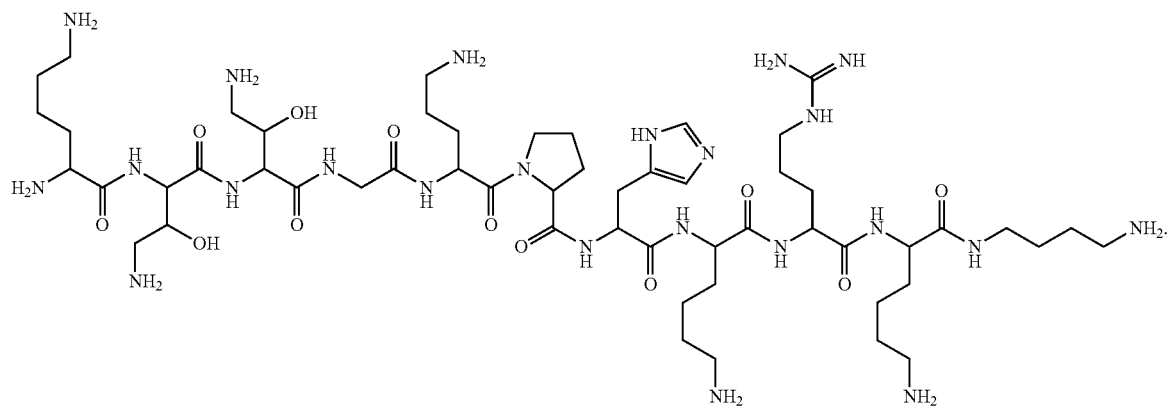

(Ic)

8. The pharmaceutical composition of claim 1 comprising a pharmaceutically acceptable carrier.

9. The pharmaceutical composition according to claim 1 wherein the aminoglycoside antibiotic compound is kanamycin or gentamicin.

* * * * *